(12) United States Patent
Nance et al.

(10) Patent No.: US 7,780,692 B2
(45) Date of Patent: Aug. 24, 2010

(54) EXPANDABLE PERCUTANEOUS SHEATH

(75) Inventors: Edward J. Nance, Corona, CA (US);
Joseph Bishop, Menifee, CA (US); Jay Lenker, Laguna Beach, CA (US);
Onnik Tchulluian, Carlsbad, CA (US);
George F. Kick, Casa Grande, AZ (US)

(73) Assignee: Onset Medical Corporation, Irvine, CA (US)

( * ) Notice: Subject to any disclaimer, the term of this patent is extended or adjusted under 35 U.S.C. 154(b) by 1555 days.

(21) Appl. No.: 10/884,017

(22) Filed: Jul. 2, 2004

(65) Prior Publication Data

US 2005/0125021 A1 Jun. 9, 2005

Related U.S. Application Data

(63) Continuation-in-part of application No. 10/728,728, filed on Dec. 5, 2003.

(51) Int. Cl.
*A61M 29/00* (2006.01)
(52) U.S. Cl. ....................................... 606/198
(58) Field of Classification Search .......... 606/192, 606/198; 604/104, 164.05
See application file for complete search history.

(56) References Cited

U.S. PATENT DOCUMENTS

| | | | |
|---|---|---|---|
| 319,296 | A | 6/1885 | Molesworth |
| 668,879 | A | 2/1901 | Miller |
| 1,213,001 | A | 1/1917 | Philips |
| 1,248,492 | A | 12/1917 | Hill |
| 2,548,602 | A | 4/1948 | Greenburg |
| 3,509,883 | A | 5/1970 | Dibelius |
| 3,545,443 | A | 12/1970 | Ansari |
| 3,742,958 | A | 7/1973 | Rundles |
| 3,789,852 | A | 2/1974 | Kim et al. |
| 3,902,492 | A | 9/1975 | Greenhalgh |
| 4,018,230 | A | 4/1977 | Ochiai et al. |
| 4,141,364 | A | 2/1979 | Schultze |
| 4,338,942 | A | 7/1982 | Fogarty |
| 4,401,433 | A | 8/1983 | Luther |
| 4,411,655 | A | 10/1983 | Schreck |
| 4,451,256 | A | 5/1984 | Weikl et al. |

(Continued)

FOREIGN PATENT DOCUMENTS

EP 0177177 4/1986

(Continued)

OTHER PUBLICATIONS

Jun. 15, 2006 International Preliminary Report in Int'l App. No. PCT/US2004/040651 filed on Dec. 3, 2004.

(Continued)

*Primary Examiner*—Anhtuan T Nguyen
*Assistant Examiner*—Sarah A Simpson
(74) *Attorney, Agent, or Firm*—Knobbe Martens Olson & Bear, LLP.

(57) ABSTRACT

Disclosed is an expandable percutaneous sheath, for introduction into the body while in a first, low cross-sectional area configuration, and subsequent expansion to a second, enlarged cross-sectional configuration. The sheath is maintained in the first, low cross-sectional configuration by a tubular restraint. In one application, the sheath is utilized to provide access for a diagnostic or therapeutic procedure such as percutaneous nephrostomy or urinary bladder access.

15 Claims, 19 Drawing Sheets

U.S. PATENT DOCUMENTS

| | | | |
|---|---|---|---|
| 4,479,497 A | 10/1984 | Fogarty et al. | |
| 4,581,025 A | 4/1986 | Timmermans | |
| 4,589,868 A | 5/1986 | Dretler | |
| 4,601,713 A | 7/1986 | Fuqua | |
| 4,610,688 A | 9/1986 | Silvestrini et al. | |
| 4,636,346 A | 1/1987 | Gold et al. | |
| 4,650,466 A | 3/1987 | Luther | |
| 4,710,181 A | 12/1987 | Fuqua | |
| 4,716,901 A | 1/1988 | Jackson et al. | |
| 4,738,666 A | 4/1988 | Fuqua | |
| 4,739,762 A | 4/1988 | Palmaz | |
| 4,772,266 A | 9/1988 | Groshong | |
| 4,790,817 A | 12/1988 | Luther | |
| 4,798,193 A | 1/1989 | Giesy et al. | |
| 4,846,791 A | 7/1989 | Hattler et al. | |
| 4,865,593 A | 9/1989 | Ogawa et al. | |
| 4,869,717 A | 9/1989 | Adair | |
| 4,884,573 A | 12/1989 | Wijay et al. | |
| 4,888,000 A | 12/1989 | McQuilkin et al. | |
| 4,896,669 A | 1/1990 | Bhate et al. | |
| 4,898,591 A | 2/1990 | Jang et al. | |
| 4,899,729 A | 2/1990 | Gill et al. | |
| 4,921,479 A | 5/1990 | Grayzel | |
| 4,954,126 A | 9/1990 | Wallsten | |
| 4,955,895 A | 9/1990 | Sugiyama et al. | |
| 4,972,827 A | 11/1990 | Kishi et al. | |
| 4,984,564 A | 1/1991 | Yuen | |
| 4,986,830 A | 1/1991 | Owens et al. | |
| 5,011,488 A | 4/1991 | Ginsburg et al. | |
| 5,045,056 A | 9/1991 | Behl | |
| 5,057,092 A | 10/1991 | Webster, Jr. | |
| 5,059,183 A | 10/1991 | Semrad | |
| 5,066,285 A | 11/1991 | Hillstead | |
| 5,078,736 A | 1/1992 | Behl | |
| 5,092,839 A | 3/1992 | Kipperman | |
| 5,098,393 A | 3/1992 | Amplatz et al. | |
| 5,100,388 A | 3/1992 | Behl et al. | |
| 5,108,416 A | 4/1992 | Ryan et al. | |
| 5,112,304 A | 5/1992 | Barlow et al. | |
| 5,116,318 A | 5/1992 | Hillstead | |
| 5,122,122 A | 6/1992 | Allgood | |
| 5,139,511 A | 8/1992 | Gill et al. | |
| 5,147,316 A | 9/1992 | Castillenti | |
| 5,158,545 A | 10/1992 | Trudell et al. | |
| 5,163,903 A | 11/1992 | Crittenden et al. | |
| 5,176,659 A | 1/1993 | Mancini | |
| 5,183,464 A | 2/1993 | Dubrul et al. | |
| 5,188,602 A | 2/1993 | Nichols | |
| 5,201,756 A | 4/1993 | Horzewski et al. | |
| 5,222,938 A | 6/1993 | Behl | |
| 5,222,971 A | 6/1993 | Willard et al. | |
| 5,234,425 A | 8/1993 | Fogarty et al. | |
| 5,250,025 A | 10/1993 | Sosnowski et al. | |
| 5,250,033 A | 10/1993 | Evans et al. | |
| 5,256,150 A | 10/1993 | Quiachon et al. | |
| 5,275,611 A | 1/1994 | Behl | |
| 5,279,553 A | 1/1994 | Winkler et al. | |
| 5,295,994 A | 3/1994 | Bonutti | |
| 5,312,360 A | 5/1994 | Behl | |
| 5,312,417 A | 5/1994 | Wilk | |
| 5,316,360 A | 5/1994 | Feikema | |
| 5,320,611 A | 6/1994 | Bonutti et al. | |
| 5,324,261 A | 6/1994 | Amundson et al. | |
| 5,392,766 A | 2/1995 | Masterson et al. | |
| 5,395,349 A | 3/1995 | Quiachon et al. | |
| 5,407,430 A | 4/1995 | Peters | |
| 5,431,676 A | 7/1995 | Dubrul et al. | |
| 5,433,708 A | 7/1995 | Nichols et al. | |
| 5,447,503 A | 9/1995 | Miller | |
| 5,454,790 A | 10/1995 | Dubrul | |
| 5,460,170 A | 10/1995 | Hammerslag | |
| 5,514,091 A | 5/1996 | Yoon | |
| 5,527,336 A | 6/1996 | Rosenbluth | |
| 5,540,658 A | 7/1996 | Evans et al. | |
| 5,542,928 A | 8/1996 | Evans et al. | |
| 5,573,520 A | 11/1996 | Schwartz | |
| 5,647,857 A | 7/1997 | Anderson et al. | |
| 5,657,963 A | 8/1997 | Hincliffe et al. | |
| 5,662,614 A | 9/1997 | Edoga | |
| 5,702,373 A | 12/1997 | Samson | |
| 5,709,713 A | 1/1998 | Evans et al. | |
| 5,766,203 A | 6/1998 | Imran et al. | |
| 5,776,141 A | 7/1998 | Klein et al. | |
| 5,810,776 A * | 9/1998 | Bacich et al. | 604/131 |
| 5,902,282 A * | 5/1999 | Balbierz | 604/264 |
| 5,908,435 A | 6/1999 | Samuels | |
| 5,961,499 A | 10/1999 | Bonutti et al. | |
| 5,964,730 A | 10/1999 | Williams et al. | |
| 6,030,364 A | 2/2000 | Durgin et al. | |
| 6,056,718 A | 5/2000 | Funderburk et al. | |
| 6,063,056 A | 5/2000 | Engelberg | |
| 6,080,174 A | 6/2000 | Dubrul et al. | |
| 6,168,579 B1 | 1/2001 | Tsugita | |
| 6,183,443 B1 | 2/2001 | Kratoska et al. | |
| 6,187,000 B1 | 2/2001 | Davison et al. | |
| 6,197,016 B1 | 3/2001 | Fourkas et al. | |
| 6,248,116 B1 | 6/2001 | Chevillon et al. | |
| 6,280,452 B1 | 8/2001 | Mears | |
| 6,312,443 B1 | 11/2001 | Stone | |
| 6,358,238 B1 | 3/2002 | Sherry | |
| 6,443,979 B1 | 9/2002 | Stalker et al. | |
| 6,447,540 B1 | 9/2002 | Fontaine et al. | |
| 6,494,860 B2 | 12/2002 | Rocamora et al. | |
| 6,494,893 B2 | 12/2002 | Dubrul et al. | |
| 6,517,551 B1 | 2/2003 | Driskill | |
| 6,524,320 B2 | 2/2003 | DiPoto | |
| 6,537,247 B2 | 3/2003 | Shannon | |
| 6,613,038 B2 | 9/2003 | Bonutti et al. | |
| 6,616,678 B2 | 9/2003 | Nishtala et al. | |
| 6,638,268 B2 | 10/2003 | Niazi | |
| 6,706,017 B1 | 3/2004 | Dulguerov | |
| 6,808,520 B1 | 10/2004 | Fourkas et al. | |
| 6,951,555 B1 | 10/2005 | Suresh et al. | |
| 7,033,369 B2 | 4/2006 | Davison et al. | |
| 7,135,015 B2 | 11/2006 | Dulak et al. | |
| 7,309,334 B2 | 12/2007 | Von Hoffmann | |
| 7,316,677 B1 | 1/2008 | Dulak et al. | |
| 7,329,268 B2 | 2/2008 | Van Nguyen et al. | |
| 7,457,661 B2 | 11/2008 | Doty | |
| 2001/0012950 A1 | 8/2001 | Nishtala et al. | |
| 2001/0037126 A1 | 11/2001 | Stack et al. | |
| 2002/0009535 A1 | 1/2002 | Michal et al. | |
| 2002/0010440 A1 | 1/2002 | Segesser | |
| 2002/0010476 A1 | 1/2002 | Mulholland et al. | |
| 2002/0077653 A1 | 6/2002 | Hudson et al. | |
| 2002/0099431 A1* | 7/2002 | Armstrong et al. | 623/1.11 |
| 2002/0161377 A1* | 10/2002 | Rabkin | 606/108 |
| 2003/0050600 A1 | 3/2003 | Ressemann et al. | |
| 2003/0195551 A1 | 10/2003 | Davison et al. | |
| 2003/0212384 A1 | 11/2003 | Hayden | |
| 2003/0216770 A1 | 11/2003 | Persidsky et al. | |
| 2004/0006344 A1 | 1/2004 | Nguyen et al. | |
| 2004/0236346 A1 | 11/2004 | Parker | |
| 2005/0085842 A1 | 4/2005 | Eversull et al. | |
| 2005/0124937 A1 | 6/2005 | Kick et al. | |
| 2005/0149105 A1 | 7/2005 | Leeflang et al. | |
| 2005/0222576 A1 | 10/2005 | Kick et al. | |
| 2006/0052750 A1 | 3/2006 | Lenker et al. | |
| 2006/0247602 A1 | 11/2006 | Dulak et al. | |
| 2007/0112335 A1 | 5/2007 | Dulak et al. | |

FOREIGN PATENT DOCUMENTS

| | | |
|---|---|---|
| EP | 0 249 456 | 12/1987 |

| EP | 0385920 | 9/1990 |
| EP | 0206553 | 1/1991 |
| WO | 92/19312 | 11/1992 |
| WO | 95/30374 | 11/1995 |
| WO | WO/99/17665 | 4/1999 |
| WO | WO 03/090834 A2 | 11/2003 |

OTHER PUBLICATIONS

Jan. 30, 2008 European Patent Office Communication in Euro. App. No. 04 813 043.9 filed on Dec. 3, 2004.

Aug. 11, 2008 Response to Jan. 30, 2008 European Patent Office Communication in Euro. App. No. 04 813 043.9 filed on Dec. 3, 2004.

Sep. 13, 2006 Non-final Rejection in U.S. Appl. No. 10/728,728, filed Dec. 5, 2003.

Dec. 12, 2006 Response to Sep. 13, 2006 Non-final Rejection in U.S. Appl. No. 10/728,728, filed Dec. 5, 2003.

May 1, 2007 Notice of Allowance in U.S. Appl. No. 10/728,728, filed Dec. 5, 2003.

Oct. 18, 2007 Non-final Rejection in U.S. Appl. No. 10/728,728, filed Dec. 5, 2003.

Jan. 18, 2008 Response to Oct. 18, 2007 Non-final Rejection in U.S. Appl. No. 10/728,728, filed Dec. 5, 2003.

May 28, 2008 Non-final Rejection in U.S. Appl. No. 10/728,728, filed Dec. 5, 2003.

Nov. 25, 2008 Response to May 28, 2008 Non-final Rejection in U.S. Appl. No. 10/728,728, filed Dec. 5, 2003.

Feb. 19, 2009 Final Rejection in U.S. Appl. No. 10/728,728, filed Dec. 5, 2003.

Jan. 10, 2007 Non-final Rejection in U.S. Appl. No. 11/415,659, filed on May 2, 2006.

Jun. 11, 2007 Response to Jan. 10, 2007 Non-final Rejection in U.S. Appl. No. 11/415,659, filed May 2, 2006.

Aug. 20, 2007 Final Rejection in U.S. Appl. No. 11/415,659, filed May 2, 2006.

Nov. 7, 2007 Response to Aug. 20, 2007 Final Rejection in U.S. Appl. No. 11/415,659, filed May 2, 2006.

Nov. 16, 2007 Advisory Action in U.S. Appl. No. 11/415,659, filed May 2, 2006.

Feb. 20, 2008 Response to Aug. 20, 2007 Final Rejection in U.S. Appl. No. 11/415,659, filed May 2, 2006.

May 20, 2008 Non-final Rejection in U.S. Appl. No. 11/415,659, filed May 2, 2006.

Nov. 19, 2008 Response to May 20, 2008 Non-final Rejection in U.S. Appl. No. 11/415,659, filed May 2, 2006.

Apr. 6, 2009 Final Rejection in U.S. Appl. No. 11/415,659, filed May 2, 2006.

May 11, 2009 Response to Apr. 6, 2009 Final Rejection in U.S. Appl. No. 11/415,659, filed May 2, 2006.

Jan. 8, 2007 Non-final Rejection in U.S. Appl. No. 11/415,764, filed May 2, 2006.

Jun. 8, 2007 Response to Jan. 8, 2007 Non-final Rejection in U.S. Appl. No. 11/415,764, filed May 2, 2006.

Aug. 20, 2007 Non-final Rejection in U.S. Appl. No. 11/415,764, filed May 2, 2006.

Feb. 20, 2008 Response to Aug. 20, 2007 Non-final Rejection in U.S. Appl. No. 11/415,764, filed May 2, 2006.

Jun. 13, 2008 Non-final Rejection in U.S. Appl. No. 11/415,764, filed May 2, 2006.

Dec. 12, 2008 Response to Jun. 13, 2008 Non-final Rejection in U.S. Appl. No. 11/415,764, filed May 2, 2006.

Oct. 3, 2008 Non-final Rejection in U.S. Appl. No. 11/223,897, filed Sep. 9, 2005.

Feb. 3, 2009 Response to Oct. 3, 2008 Non-final Rejection in U.S. Appl. No. 11/223,897, filed Sep. 9, 2005.

Apr. 17, 2009 Final Rejection in U.S. Appl. No. 11/223,897, filed Sep. 9, 2005.

May 12, 2009 Response to Apr. 17, 2009 Final Rejection in U.S. Appl. No. 11/223,897, filed Sep. 9, 2005.

Mar. 19, 2010 Non-Final Rejection in U.S. Appl. No. 11/415,764, filed May 2, 2006.

* cited by examiner

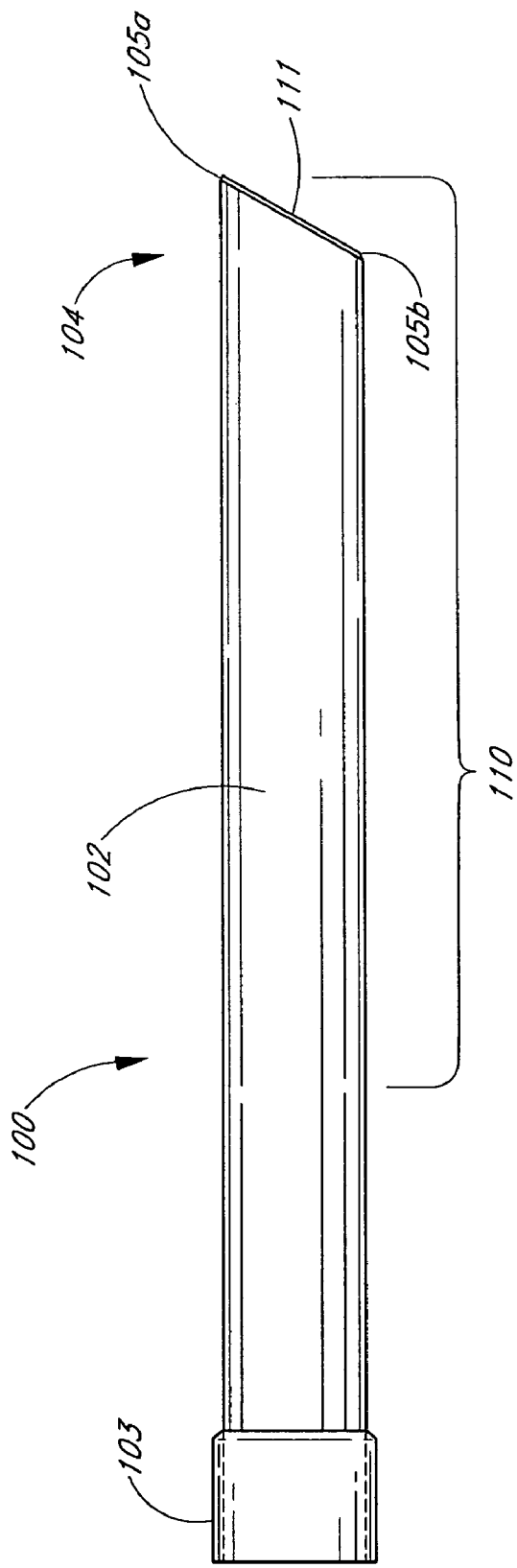
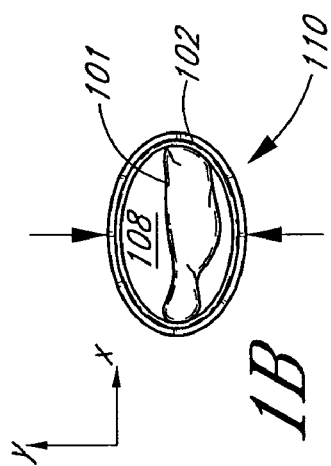
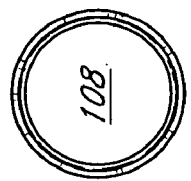
FIG. 1
FIG. 1A
FIG. 1B

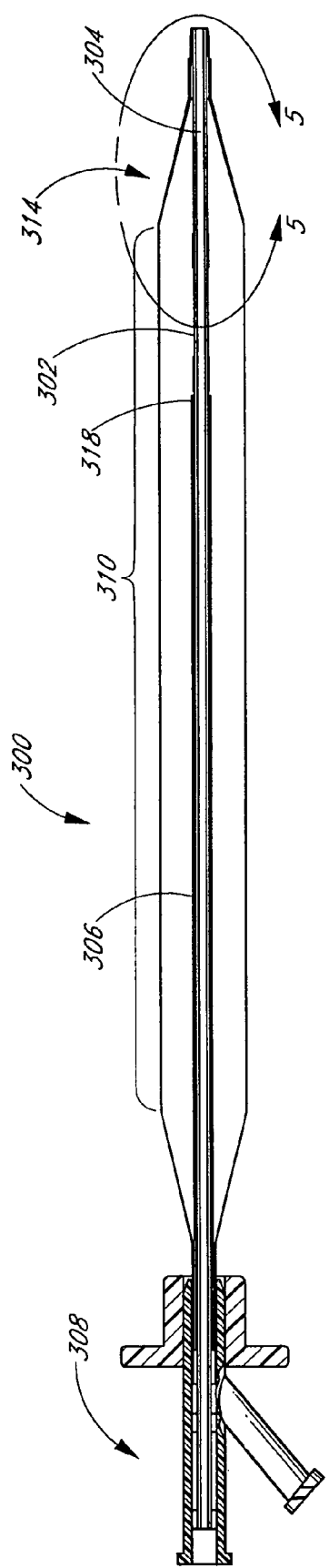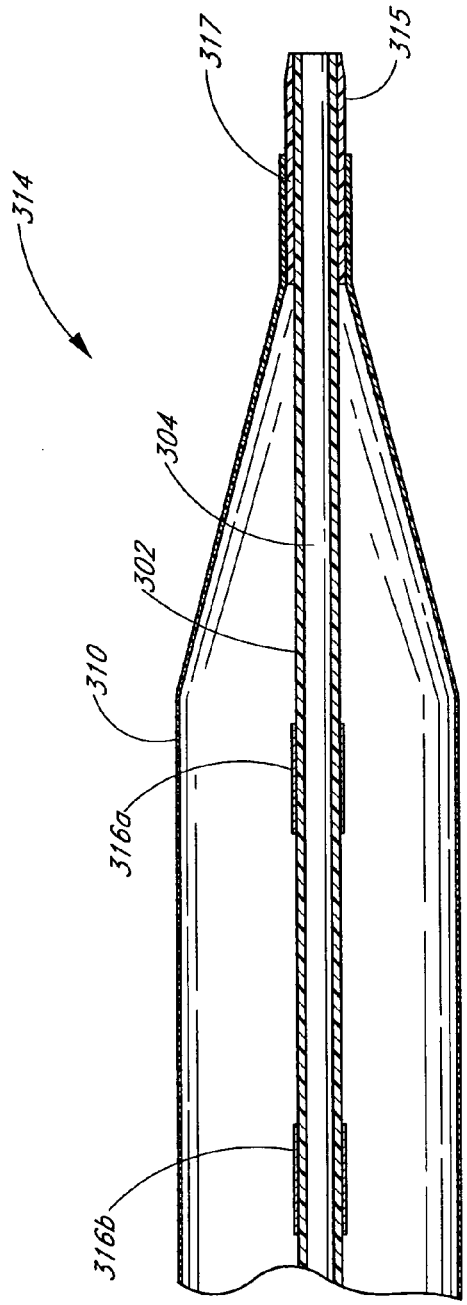
FIG. 4
FIG. 5

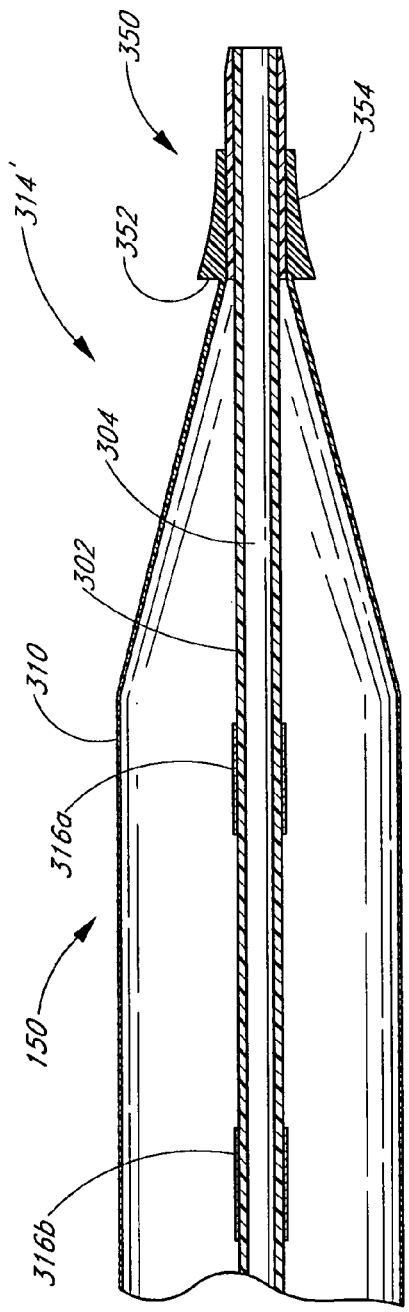
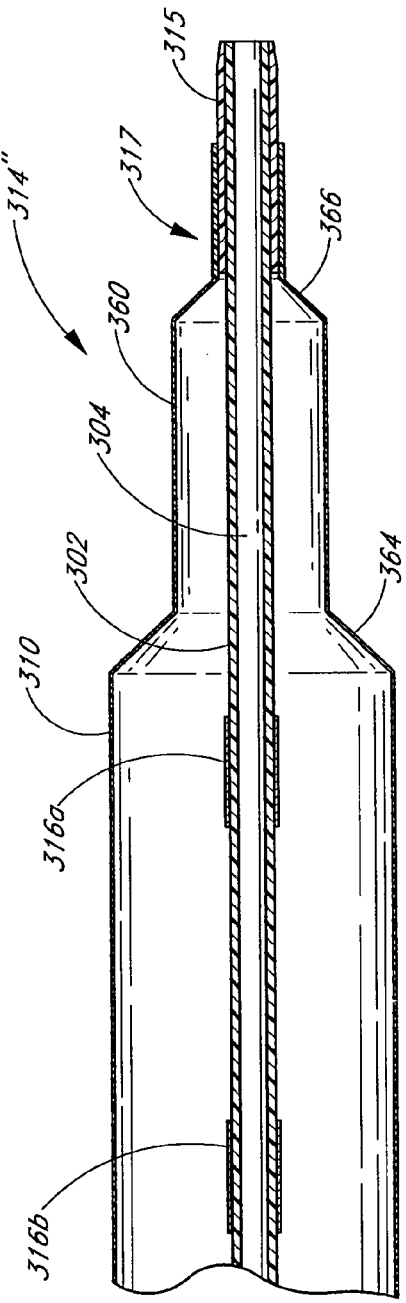
FIG. 5A
FIG. 5B

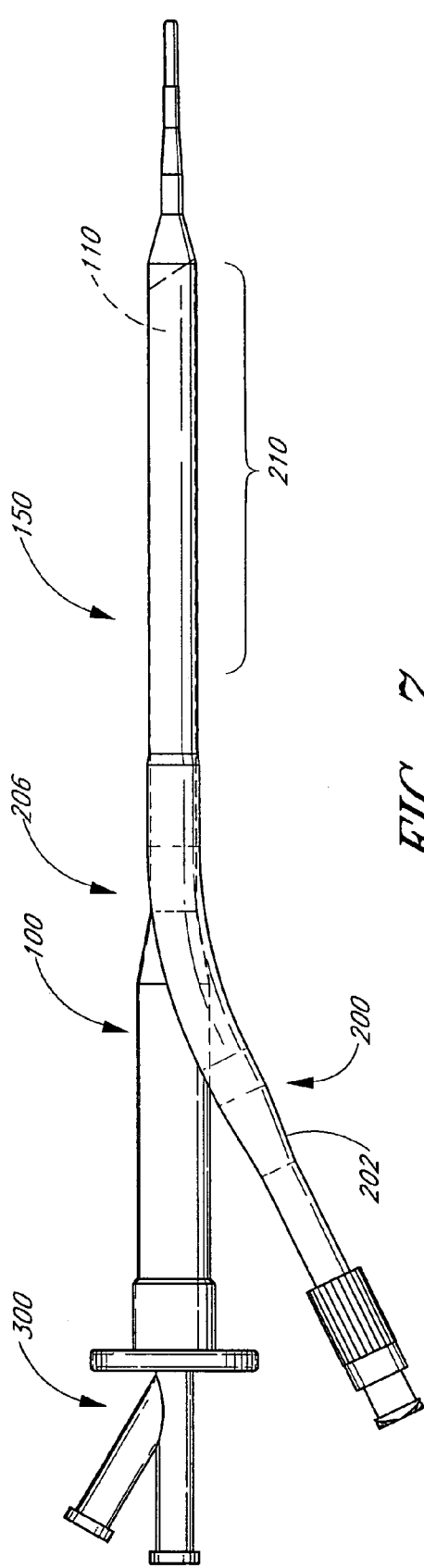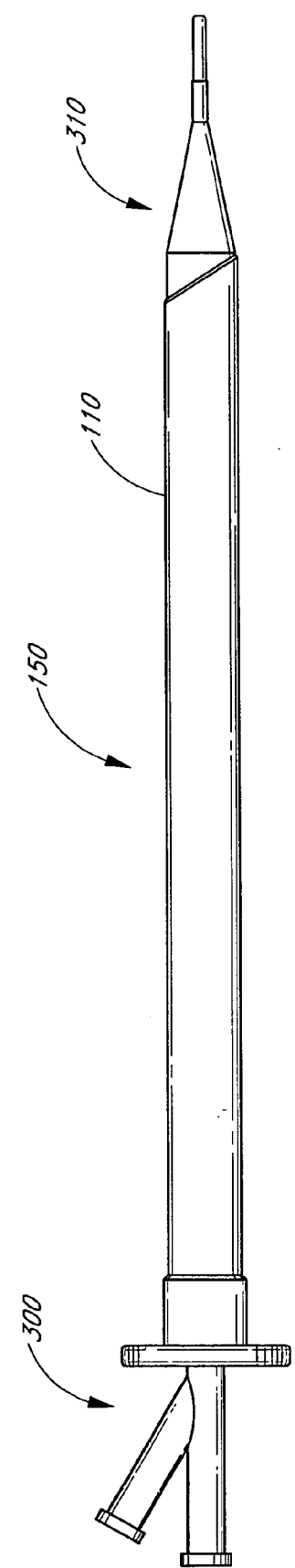
FIG. 7
FIG. 8

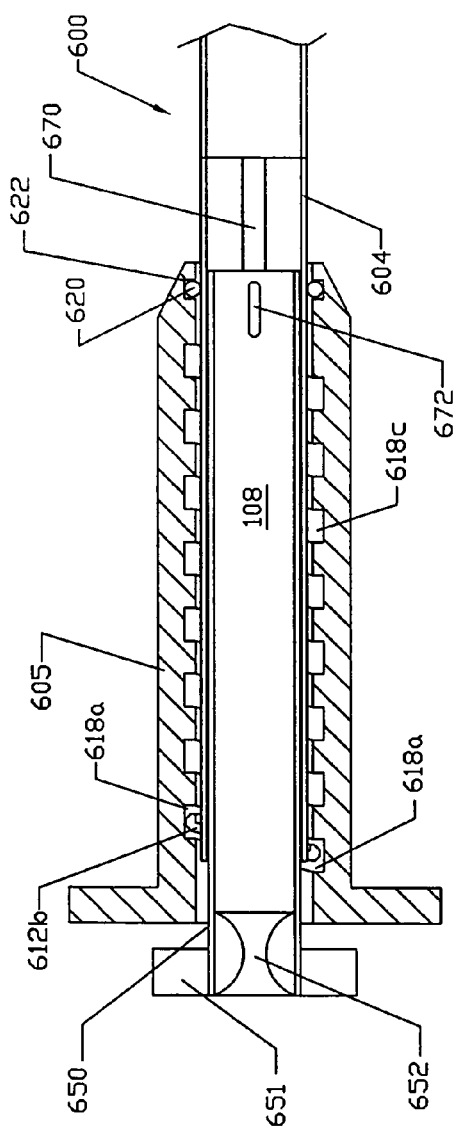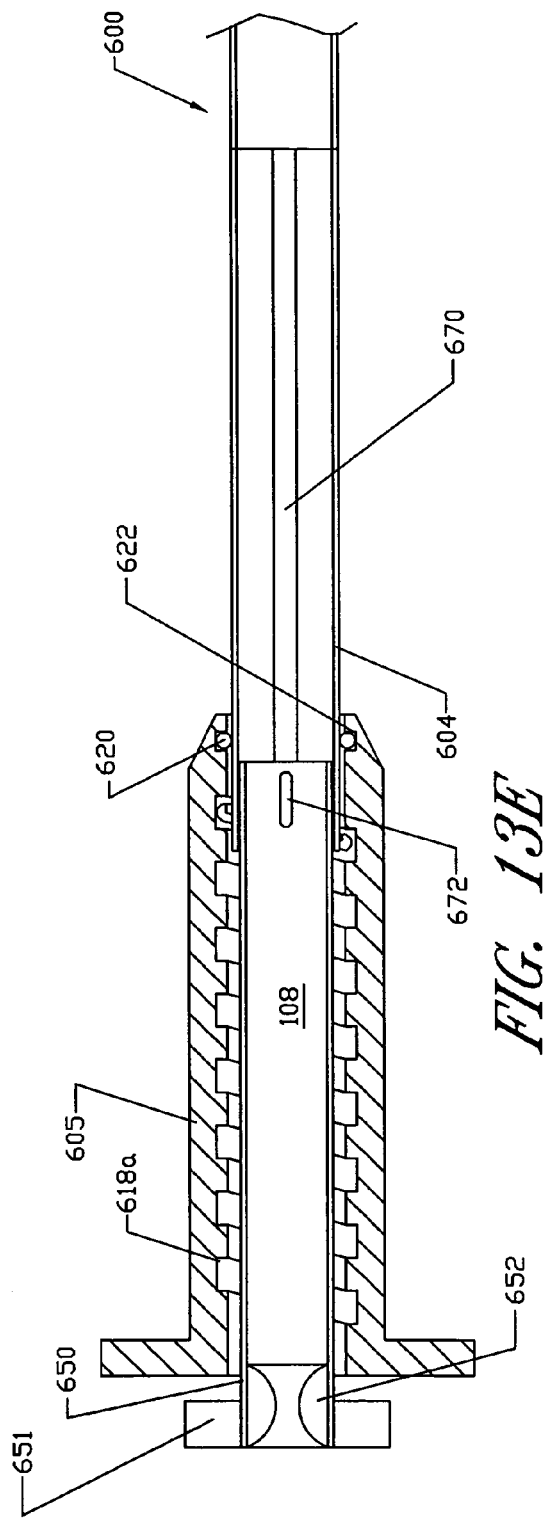

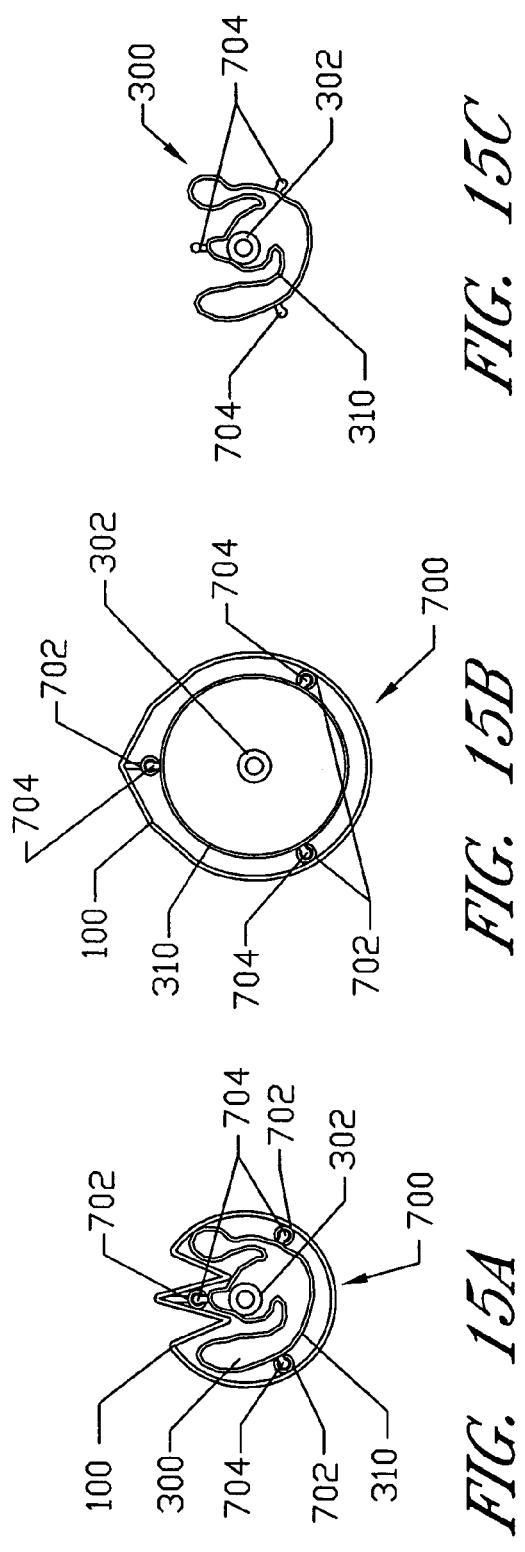

EXPANDABLE PERCUTANEOUS SHEATH

PRIORITY INFORMATION

This application is a continuation-in-part of U.S. patent application Ser. No. 10/728,728, filed Dec. 5, 2003.

BACKGROUND OF THE INVENTION

1. Field of the Invention

The present invention relates to medical devices and, more particularly, to methods and devices for forming a percutaneous channel. In one application, the present invention relates to methods and devices for providing percutaneous access to a soft tissue or organ.

2. Description of the Related Art

A wide variety of diagnostic or therapeutic procedures involves the introduction of a device through a natural or artificially created access pathway. A general objective of access systems, which have been developed for this purpose, is to minimize the cross-sectional area of the puncture, while maximizing the available space for the diagnostic or therapeutic instrument. These procedures include, among others, a wide variety of laparoscopic diagnostic and therapeutic interventional procedures.

Percutaneous nephrostomy is an example of one type of therapeutic interventional procedure that requires an artificially created pathway. Percutaneous nephrostomy is a minimally invasive procedure that can be used to provide percutaneous access to the upper urinary tract. At first, percutaneous nephrostomy was used only for urinary diversion but now it may be used for more complex procedures such as stone extraction, integrate endopyelotomy, and resection of transitional cell carcinoma of the upper urinary tract.

In many percutaneous nephrostomy systems, a stiff guidewire is first placed into the renal collection system through the renal parenchyma and the ureter using fluoroscopic control. A second "safety wire" may be placed with a dual lumen catheter for maintaining the tract should the first wire become dislodged or kinked.

Once guidewire control is established, a dilator sheath is used to create the tract and establish a rigid working lumen. An early technique involved advancing a flexible, 8 French, tapered catheter over the first guidewire to provide guidewire protection as well as a stable path for the placement of larger diameter dilators and sheaths. The larger diameter sheaths are sequentially advanced over the catheter and each other until an approximately 34 French (11 to 12 mm diameter) tract is established. The inner sheaths or dilators may then be sequentially removed such that the outermost sheath defines a working lumen. In this system, tract formation is accomplished by the angular shearing force of each subsequent sheath placement, which cuts a path through the tissue. Because axial pressure is required to advance and place each sheath, care must be taken to avoid kinking the tapered catheter and/or advancing the sheaths to far and perforating the renal pelvis. This technique also requires a large number of steps.

A more recent technique utilizes a balloon that is advanced over the first guide wire. Once in place in the renal pelvis, the balloon is inflated with a dilute contrast media solution to enlarge the tract. Once the balloon is inflated to a suitable diameter, a rigid sheath is advanced over the balloon. Advancing the rigid sheath over the balloon typically requires applying axial force to the sheath as well as rotation of the sheath relative to the balloon. The balloon may then be deflated and removed from the rigid sheath so that the rigid sheath may define a working lumen. In general, this technique is considered less traumatic than the previously described technique. Nevertheless, placement of the rigid sheath still involves angular shearing forces and several steps.

Additional information regarding percutaneous nephrostomy can be found in McDougall, E. M., et al. (2002), Percutaneous Approaches to the Upper Urinary Tract, *Campbell's Urology*, 8th ed, vol. 4, pp. 3320-3357, Chapter 98, Philadelphia, Saunders.

A need therefore remains for improved access technology, which allows a device to be percutaneously passed through a small diameter tissue tract, while accommodating the introduction of relatively large diameter instruments.

SUMMARY OF THE INVENTION

One embodiment of the present invention comprises a percutaneous access system for providing minimally invasive access. The system includes an access sheath comprising an elongate tubular body that defines a lumen, at least a portion of the elongate tubular body being expandable from a first, folded, smaller cross-sectional profile to a second, greater cross-sectional profile. A releasable jacket is carried by the access sheath to restrain at least a portion of the elongate tubular structure in the first, folded, smaller cross-sectional profile. The elongate tubular body is sufficiently pliable to allow the passage of objects having a maximum cross-sectional dimension that is larger than an inner diameter a circle corresponding to the cross-sectional area of the elongate tubular body in the second, greater cross-sectional profile.

In another embodiment of the present invention, a percutaneous access system for providing minimally invasive access includes an introduction sheath comprising an elongate tubular body having a proximal end and a distal end and defining a first axial lumen. At least a portion of the elongate tubular body is expandable from a first, smaller cross-sectional profile to a second, greater cross-sectional profile. A releasable jacket is carried by the access sheath to restrain at least a portion of the elongate tubular member in the first, smaller cross-sectional profile. An extender comprises an elongate tubular structure, which defines a second axial lumen. Complementary structures are provided in between the elongate tubular body and the extender. The complementary structures provide a selectively releaseable connection between the elongate tubular body and the extender to place the first axial lumen in communication with the second axial lumen.

In another embodiment of the present invention, a percutaneous access sheath assembly for providing minimally invasive access comprises an access sheath that includes an elongate tubular member having a proximal end and a distal end and defining a working lumen. At least a portion of the elongate tubular member is expandable from a first, folded, smaller cross-sectional profile to a second, greater cross-sectional profile. A releasable jacket is carried by the access sheath to restrain at least a portion of the elongate tubular member in the first, smaller cross-sectional profile. An extender comprises an inner tubular member and an outer tubular member that is positioned over the inner tubular member. The inner member and outer member are moveable between a first position in which the inner and outer member overlap such that the extender has a first, shorter axial length and a second position in which the overlap between the inner and outer members is reduced and the extender has a second, longer axial length.

In another embodiment of the present invention, a percutaneous access system, for providing minimally invasive access includes an elongate tubular body that defines an lumen, at least a portion of the elongate tubular body being expandable from a first, folded, smaller cross-sectional profile to a second, greater cross-sectional profile. A releasable restraint is carried by the access sheath to restrain at least a portion of the elongate tubular structure in the first, smaller cross-sectional profile. An expandable member is positioned within the elongate tubular body and configured to expand the elongate tubular body from the first, smaller cross-sectional profile to the second, greater cross-sectional profile. A stop is provided to limit distal movement of the releasable restraint as the elongate tubular body expands.

In another embodiment of the present invention, a percutaneous access assembly includes an elongate tubular body that defines a lumen. At least a portion of the elongate tubular structure is expandable from a first, folded, smaller cross-sectional profile to a second, greater cross-sectional profile. A releasable jacket is carried by the access sheath to restrain at least a portion of the elongate tubular body in the first, smaller cross-sectional profile. In the first, folded, smaller-cross-sectional profile, the elongate tubular body includes creased sections that are positioned on the outer periphery of the tubing and generally face each other.

In another embodiment of the present invention, a percutaneous access sheath system includes an elongate tubular structure that defines an lumen, at least a portion of the elongate tubular structure being expandable from a first, folded, smaller cross-sectional profile to a second, greater cross-sectional profile. A releasable jacket is carried by the access sheath to restrain at least a portion of the elongate tubular structure in the first, smaller cross-sectional profile. A guidewire is positioned between the elongate tubular structure and the releasable jacket.

In another embodiment of the present invention, a method of providing percutaneous access comprises inserting a guidewire into a patient, percutaneously inserting an elongate tubular body having a first, smaller cross-sectional profile over the guidewire; expanding the elongate tubular body with an expandable member from the first, smaller cross-sectional profile to a second, greater cross-sectional profile, releasing the elongate tubular body from a constraining tubular jacket, removing the expandable member from the elongate tubular body; collapsing the elongate tubular body to a cross-sectional profile smaller than the second, greater cross-sectional profile, and removing the elongate tubular body from the patient.

In another embodiment of the present invention, a percutaneous access sheath system comprises an elongate tubular body that defines a lumen. At least a portion of the elongate tubular structure is expandable from a first, folded, smaller cross-sectional profile to a second, greater cross-sectional profile. A jacket is removably carried by the access sheath to restrain at least a portion of the elongate tubular body in the first, smaller cross-sectional profile. A collapsible member is configured to be inserted into the elongate tubular body when the elongate tubular body is in the second, greater cross-sectional profile. A first coupling structure is provided on the collapsible member and a second complementary coupling structure is provided on the elongate tubular body for radially coupling the collapsible member to the elongate tubular body.

In one embodiment where the percutaneous access sheath is used to provide access to the upper urinary tract, the percutaneous access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder Other applications of the percutaneous access sheath include a variety of diagnostic or therapeutic clinical situations, which require access to the inside of the body, through either an artificially created or natural body lumen.

BRIEF DESCRIPTION OF THE DRAWINGS

FIG. 1 is a side elevational view of a percutaneous access sheath;

FIG. 1A is a front view of the percutaneous access sheath;

FIG. 1B is a front view of the percutaneous access sheath with an unsymmetrical object being is passed therethrough;

FIG. 4 is a side elevational view of an access sheath expansion balloon catheter;

FIG. 5 is an enlarged view of the distal end of the expansion balloon catheter;

FIG. 5A is an enlarged view of a modified embodiment of the distal end of the expansion balloon catheter;

FIG. 5B is an enlarged view of another modified embodiment of the distal end of the expansion balloon catheter;

FIG. 7 illustrates the percutaneous access sheath assembly, with the expansion balloon catheter inserted into the structure illustrated in FIG. 3;

FIG. 8 illustrates the percutaneous access sheath assembly of FIG. 7 in an expanded configuration and the jacket removed;

FIG. 13D illustrates the proximal end of the percutaneous access sheath assembly as in FIG. 7 with another embodiment of a telescoping member;

FIG. 13E illustrates the proximal end of the percutaneous access sheath assembly of FIG. 13D in an extended position;

FIG. 15A is a cross-sectional view of a modified embodiment of the percutaneous access sheath assembly of FIG. 7 in an compressed configuration;

FIG. 15B is a cross-sectional view of the percutaneous access sheath assembly of FIG. 15A in an expanded configuration;

FIG. 15C is a cross-sectional view of an expansion device of the percutaneous access sheath assembly of FIG. 15A in a compressed configuration;

FIG. 15D is a cross-sectional view an access sheath of the percutaneous access sheath assembly of FIG. 15A in an expanded configuration; and FIG. 15E is a cross-sectional view of the expansion device of FIG. 15C in an expanded configuration.

DETAILED DESCRIPTION OF THE PREFERRED EMBODIMENTS

Figure 2:
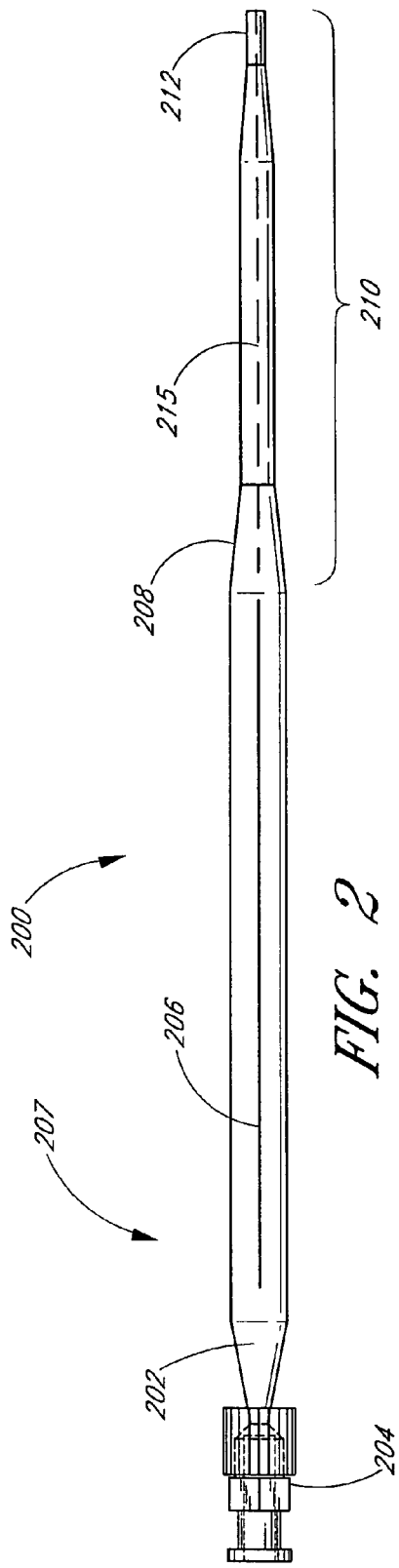
FIG. 2 is a side elevational view of a jacket.

FIG. 1 is an overview of an exemplary embodiment of a percutaneous access sheath 100. The sheath 100 generally comprises an elongate tubular body 102 with an axial lumen 108 (FIG. 1A), and is designed to provide percutaneous access to a site in the body for the purpose of diagnosis or treatment.

In the exemplary embodiment, the elongate tubular body 102 has a distal section 110 and a proximal section 103. As shown in FIG. 1, the proximal section 103 may have a slightly larger inner and outer diameter as compared to the distal section 110. As will be explained in more detail below, the proximal section 103 may be used to secure the access sheath 100 to a connector. With continued reference to FIG. 1, the distal end 104 of the distal section 110 may be provided with a beveled distal face 111, which preferably forms an angle of about 45 to about 75 degrees with respect a longitudinal axis of the tubular body 102. In this manner, the distal face 111 forms a leading edge 105a and a trailing edge 105b. As will be explained below, during insertion, the beveled face 111 advantageously provides the distal end 104 of the access sheath 100 with a smaller cross-sectional profile in a compressed configuration. This provides a smoother transition from the distal end 104 of the access sheath 100 to the deployment catheter (described below). In addition, in the expanded configuration, the leading edge 105a maintains positional purchase within the target tissue or organ while the trailing edge 105b provides the sheath 100 with an aperture to facilitate instrument maneuvering and visualization within the internal structure of the tissue or organ under examination or treatment. In a modified embodiment, the distal face 111 may form an angle of about 90 degrees with respect to the longitudinal axis of the tubular body.

The length and diameter of the sheath 100 can be varied according to clinical need, as will be understood by those skilled in the art with reference to this disclosure. In one exemplary embodiment for percutaneous nephrostomy, the access sheath 100 has an overall length of about 17 to about 30 centimeters with the distal section 110 having a length of about 11 to about 24 centimeters. As will be explained in more detail below, a portion or all of the distal section 110 is expandable from a first, smaller cross-sectional profile to a second, larger cross-sectional profile. The first, smaller cross-sectional profile of the distal section 110 eases its insertion into a percutaneous treatment site. After insertion, the distal section 110 is expanded to a second, larger cross-sectional profile to provide a larger passageway for surgical instruments to reach the percutaneous treatment site. For percutaneous nephrostomy, the smaller cross-sectional profile may have a diameter of about 15 French to about 24 French and the larger cross-sectional profile may have a diameter of about 21 French to about 40 French. In the larger cross-sectional profile, the lumen 108 may have a diameter of about 18 French to about 38 French.

In this embodiment, the distal section 110 is creased in at least two and more preferably 2 to 6 sections, most preferably 2 to 4 sections, and collapsed from a larger to a smaller cross-sectional profile to ease its insertion. As will be explained in more detail below, a jacket 200 (see FIGS. 2 and 3) preferably restrains the distal section 110 of the tubing 102 in the smaller cross-sectional profile.

Figure 3:
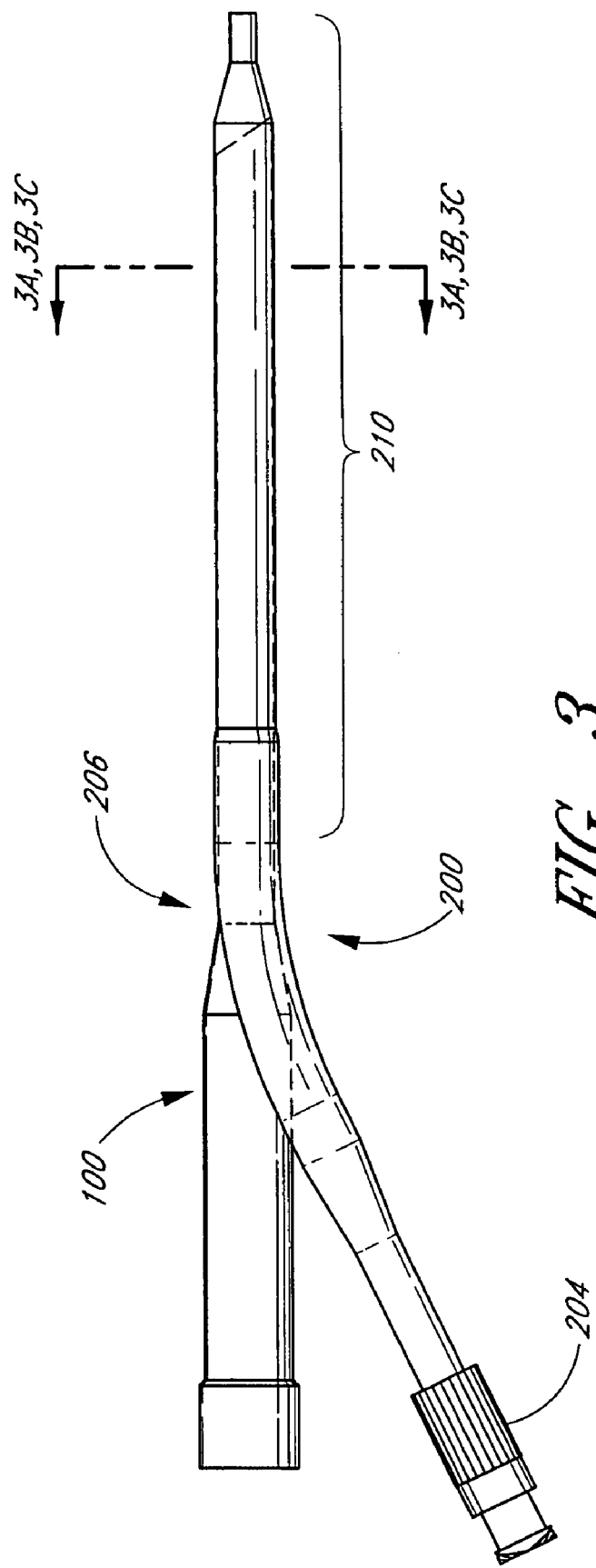
FIG. 3 illustrates the percutaneous access sheath in an axial reduced cross-sectional configuration and inserted into the jacket.
Figure 3A:
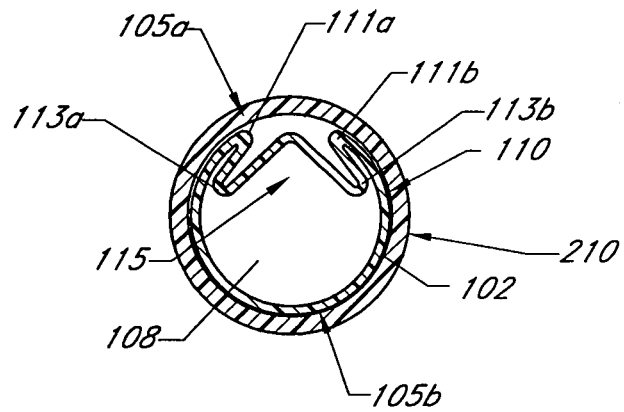
FIG. 3A is a schematic lateral cross-sectional illustration of an exemplary embodiment of a folding profile for the sheath of FIG. 3.

FIG. 3A is a lateral cross-sectional view of the sheath taken along line 3A-3A of FIG. 3 and illustrates a folding profile for collapsing the distal section 110 into a smaller cross-sectional profile. In this embodiment, the distal section 110 includes two creased outer sections 111a, 111b that lie on the perimeter of the tubing 102 and generally face each other. Two creased inner sections 113a and 113b lie within the perimeter of the tubing 102 and generally face away from each other. An additional fold or crease (not shown) may be formed on the section 115 of the tubing between the two outer creased sections 111a, 111b.

Figure 3B:
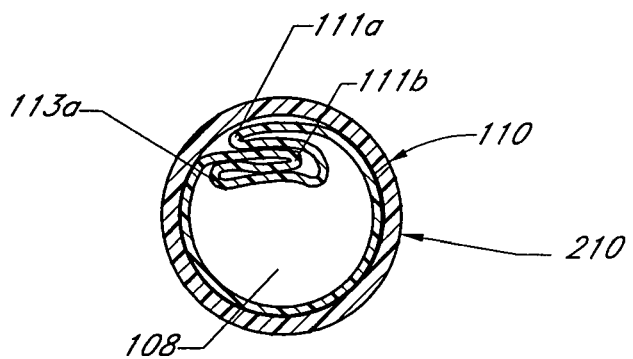
FIG. 3B is a schematic lateral cross-sectional illustration of another embodiment of a folding profile for the sheath of FIG. 3.

FIG. 3B is also a lateral cross-sectional view of the sheath taken along line 3B-3B. FIG. 3B illustrates a modified folding profile for collapsing the distal section 110 into a smaller cross-sectional profile. As shown in FIG. 3B, the outer creased sections 111a, 111b are overlapped with each other. In one embodiment, only a portion of the outer creased sections 111a, 111b are overlapped with each other. For example, the distal edge of the outer creased sections and adjacent portions may be over lapped with each other. Referring to FIGS. 3 and 3B, this arrangement reduces the cross-sectional profile of the distal end of the distal section 110 and may provide the distal end with a more tapered cross-sectional configuration to ease insertion of the sheath 100 into the patient. The peel away sleeve 210 and the collapsed working channel 108 are also shown.

Figure 2A:
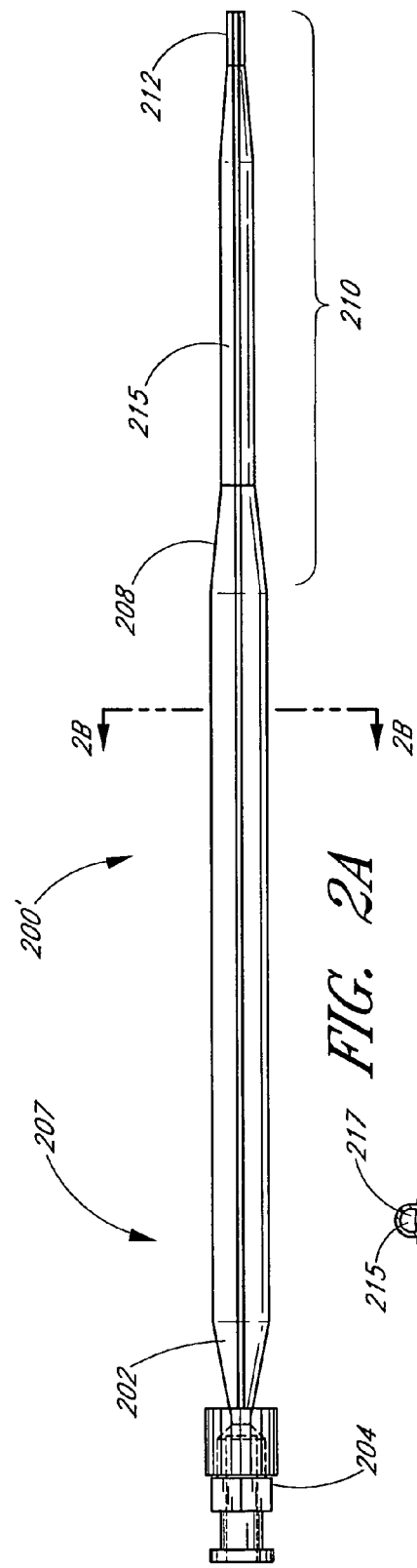
FIG. 2A is a side elevational view of a modified jacket.
Figure 3C:
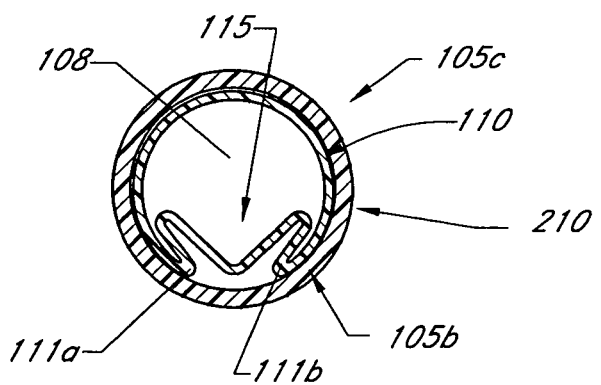
FIG. 3C is a schematic lateral cross-sectional illustration of another embodiment of a folding profile for the sheath of FIG. 3.

FIG. 3C is another lateral cross-sectional view of the sheath taken along line 3B-3B. FIG. 3B illustrates another modified embodiment for collapsing the distal section 110 of the sheath 100. This embodiment is similar to the embodiment of FIG. 3A. However, in this embodiment, the two outer creased sections 111a, 111b are positioned on the perimeter of the tubing 105b generally opposite the side of the tubing 102 on which the leading edge 105a is positioned. In contrast, in the embodiment of FIG. 2A, the two outer creased sections 111a, 111b are positioned on the perimeter of the tubing generally on the same side of the tubing 102 on which the leading edge 105a is positioned. In the collapsed configuration, the embodiment of FIG. 3C advantageously provides a more tapered profile at the distal end of the sheath 100. The embodiment of FIG. 3C may also be used in combination with the overlapped configuration described above with reference to FIG. 3B.

In one embodiment for percutaneous nephrostomy, the distal section 110 is placed into the renal collecting system through the renal parenchyma and ureters. Its length is thus determined by the anatomy and is generally in the range of about 11 cm to about 24 cm. In the illustrated embodiment, the proximal end 103 of the tubing 102 is flared and fitted onto the deployment catheter as will be explained below. The overall length of the tubing 102 depends on the distance between the insertion and treatment locations, and is generally in the range of 10-100 cm for various clinical indications. As mentioned above, for percutaneous nephrostomy, the length of the tubing is approximately 17-30 cm.

As mentioned above, in the illustrated embodiment, the percutaneous access sheath 100 comprises a length of tubing 102, which defines a lumen 108. In the expanded configuration, the tubing 102 has sufficient structural integrity to support the surrounding tissue and provide a working lumen to facilitate instrument maneuvering and visualization within the internal structure of the tissue or organ under examination or treatment. As explained below, the structural integrity of the tubing 102 is determined by a combination of factors including but not limited to, material, wall thickness to diameter ratio, yield strength, elongation at yield, and the like.

In one embodiment, the tubing 102 is also sufficiently pliable that the cross-sectional shape of the lumen 108 can change in response to the shape of objects drawn therethrough. The tubing may also be substantially inelastic, in which case the cross-sectional area of the expanded lumen remains constant, but the shape of the lumen will vary to accommodate tools (e.g., graspers) and objects (e.g., stones) advanced therethrough. This arrangement facilitates the passage of unsymmetrical objects that have a maximum cross-sectional dimension that is larger than the inner diameter of the tubing 102 in the expanded condition, so long as the greatest cross-sectional area is no greater than the cross-sectional area of the lumen 108.

FIG. 1B illustrates one arrangement where an unsymmetrical object 101 is passed through the lumen 108. In this arrangement, the tubing is substantially inelastic. As such, the cross-sectional area of the expanded lumen remains constant relative to its undistorted configuration, shown in FIG. 1A, but the tubing 102 reconfigures as the object 101 exerts an outward force against the tubing 102. Specifically, the diameter of the tubing 102 in the first direction increases as the diameter of the tubing 102 in the second direction decreases. In one embodiment, the tubing 102 may reconfigure along one or more of the creases or folds formed on the distal section 110.

In the alternative, or in combination, the tubing 102 may also compress and/or expand elastically to allow passage of an unsymmetrical object with a maximum diameter larger than the diameter of the working lumen 108. As the unsymmetrical object is passed through the lumen 108, an outwardly directed force exerted by the unsymmetrical object causes the diameter of the lumen 108 to increase along one axis while the diameter decreases along another axis to allow passage of the unsymmetrical object 101. The use of an elastic or resilient material for the tubing 102 will thus allow both the reconfiguration of lumen 108 shape as discussed above as well actual enlargement of the cross-sectional area of the lumen 108 in either a circular or non-circular profile. As the lumen 108 is reconfigured, the tubing 102 may compress and/or expand elastically along one or more of the creases or folds formed on the distal section 110.

In addition or in the alternative, the tubing 102 and associated structures are sufficiently pliable such that the access system is flexible about a longitudinal axis extending through the lumen 108. In this manner, the tubing 102 in the collapsed and/or expanded configuration may extend along a curved or nonlinear path. This is particularly advantageous if the path through the patient must bend and/or change directions to avoid a hard or rigid object (e.g., the access system is deflectable to navigate around a rib bone as the sheath 100 is advanced through the ribs). In one embodiment, the access system is sufficiently laterally flexible that the tubing 102 may flex or bend at least about 15 degrees and for some devices at least about 30 degrees from the straight longitudinal axis, under normal use conditions as described herein. In the expanded configuration, the tubing is preferably sufficiently pliable such that the tubing 102 may flex or bend about at least about 15 degrees and for some devices at least about 30 degrees from the straight longitudinal axis while preferably maintaining at least about 50% and often at least about 75% of the internal cross-sectional area in the tubing 102 as compared to the internal cross-sectional area of the tubing 102 in the expanded state in a normal straight configuration. In addition or in other embodiments, the tubing 102 may include creases, folds, hinges, transverse slots and the like which promote bending or flexing along the longitudinal axis.

The tubing is preferably also formed from a material that provides a low coefficient of friction or high lubricity. The tubing may be made out of PTFE, FEP, nylon, PEBAX, polypropylene, polyethylene, polyurethane, polyester, silicone, or other suitable materials. Alternatively, any of a variety of lubricious coatings may be applied to the inside and/or outside surface of the tubing 102, including PTFE, parylene, and others known in the art.

In one exemplary embodiment, the tubing is made out of PTFE and has a wall thickness from about 0.010 inches to about 0.024 inches. In one embodiment, configured for nephrostomy, the tubing 102 is formed from PTFE, has an outer diameter of about 33 French and a wall thickness of about 0.019 inches. The wall thickness to diameter ratio is from about 0.044 to about 1 in this embodiment. In another embodiment, suitable for ureteral access, the tubing diameter is about 0.210 inches (16 French) and the wall thickness is from about 0.009 to about 0.010 inches.

It should be appreciated that the physical properties of the tubing 102 described above represent only some optimized arrangements. Due to the interplay of the length, material, wall thickness, wall thickness to diameter ratio, yield strength, elongation at yield, number of folds and possibly other physical characteristics of the tubing, the preferred characteristics of the tubing 102 cannot be described in terms of a specific set of variables. To the contrary, changes in any one variable may be offsetable by commensurate changes in another variable, to produce an effective tubing 102 that provides one or more of the advantages described above. Such optimization can be accomplished through routine experimentation by those of skill in the art in view of the disclosure herein, and in view of the objective of providing a tubular sheath with one or more of the properties described above. In addition, the physical properties of the tubing 102 are dependent on the environment of use. For example, the structural integrity of the tubing 102 is often a function of the pressure exerted by the surrounding tissue and the temperature of the operational surroundings, which is often at or near a body temperature of 37 degrees centigrade.

FIG. 2 is an overview of the jacket 200. It is preferably made of a thin, smooth and flexible material. The jacket 200 has a proximal section 207 and a distal, restraint section 210. Referring to FIGS. 1 and 2, the restraint section 210 has a smaller cross-sectional profile than the proximal section 207 of the jacket 200. The restraint section 210 is adapted to restrain a portion or all of the distal section 110 of the percutaneous access sheath 100 in a smaller cross-sectional profile.

This is achieved by constraining the percutaneous access sheath 100 in the jacket 200 such that all or a portion of the distal section 110 of the percutaneous access sheath 100 lies within the restraint section 210 of the jacket 200.

In the illustrated embodiment, the jacket 200 may be made of heat shrink PTFE, polyethylene or other suitable materials. The proximal end 202 of the jacket 200 terminates at a pull-tab 204, which may be formed by any of a variety of structures such as, but not limited to, a grasping ring, a knob, or a threaded connector with a Luer lock at its proximal end. The jacket 200 may be provided with a slit 206 near its proximal end 202. The jacket 200 tapers at a first tapering point 208 into a restraint section 210, which tapers again into the distal tip 212. As discussed above, the restraint section 210 restrains the distal section 110 of the percutaneous access sheath 100 in its smaller cross-sectional profile. Thus the length of the restraint section 210 is approximately the same as or slightly longer or shorter than the distal section 110, and generally falls within a range of about 11-25 cm.

The outside diameter of the restraint section 210 is preferably configured to ease its insertion into a percutaneous treatment site. Depending upon the clinical application, the outside diameter may be in the range of about 3 French to about 40 French. For percutaneous nephrostomy, the outside diameter may be in the range of about 5 French to about 35 French. The restraint section 210 is configured to separate and/or tear preferably along its longitudinal axis to release the access sheath 100 as it is radially expanded. In the illustrated embodiment, the jacket 200 is perforated, scored or otherwise provided with a tear line 215 from the first tapering point 208 to its distal tip 212. In another embodiment, the jacket 200 may be constructed of a material that will disrupt or separate during expansion from the first tapering point 208 to its distal tip 212. In another embodiment, the jacket 200 may be perforated, scored or otherwise provided with a tear line for only a portion of the restraint section 210. For example, in one embodiment, the restraint section 210 may be provided with a tear line at a region close to or at the distal end of the jacket 200. This configuration may cause the jacket 200 to disrupt or separate during expansion with the expansion beginning at its distal end.

The distance between the slit 206 and the distal tip 212 is generally approximately equal to or longer than the length of the folded, compressed portion of the tubing 102 such that the folded compressed portion of the tubing 102 terminates within the restraint section 210. In one embodiment, this arrangement permits complete disruption of the jacket 200 when the access sheath 100 is fully expanded. In one embodiment, the distance between the slit 206 and the distal tip 212 is generally in the range of 6-90 cm for most clinical applications and about 11-24 cm for percutaneous nephrostomy. In the illustrated embodiment, which is configured for percutaneous nephrostomy, this distance is approximately 11 cm, and the overall length of the jacket 200 is approximately 19 cm.

Figure 2B:
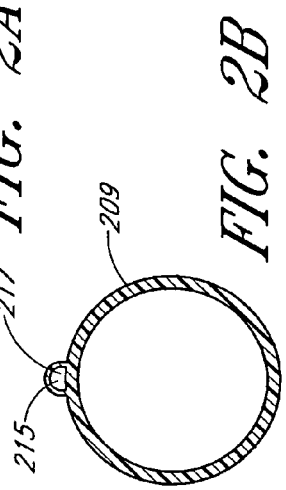
FIG. 2B is a cross sectional view of the jacket of FIG. 2A taken along line 2B-2B.

FIG. 2A illustrates a longitudinal view of a modified peel-away jacket or sleeve 200'. FIG. 2B illustrates a lateral cross-sectional view of the modified peel-away sheath 200' taken at location 2B-2B in FIG. 2A. As described above, the peel-away jacket 200 comprises a pull-tab 204, a slit (not shown), and a distal tip 212. The wall or sleeve 209 of the jacket 200 includes a channel 215, which defines an inner lumen 217 that extends from the pull-tab 204 to the distal tip 212. As will be described in more detail below, the inner lumen 217 allows passage of a secondary guidewire (not shown), which may be routed through the pull-tab 204 and out the distal tip 212. Routing the secondary guidewire through the inner lumen 217 may protect the surrounding tissue from potential damage that might be caused by the guidewire and also facilitates guidewire passage because of reduced friction. Once the peel-away jacket 200 is split apart, the guidewire remains to surround the expandable sheath 100. The inner lumen 217 may be closed as illustrated or substantially closed or open in modified embodiments.

In the embodiment shown in FIGS. 2A and 2B, the guidewire channel 215 is affixed or integral to the wall or sleeve 209 on its outer aspect. In another embodiment, the guidewire channel 215 can be affixed to the internal aspect of the wall or sleeve 209. This arrangement may provide for improved protection of the surrounding tissues from damage made by the guidewire.

FIG. 3 illustrates the percutaneous access sheath 100 inserted into the jacket 200 via the slit 206 provided near its proximal end 202. The diameter of the restraint section 210 of the jacket 200 is smaller than the diameter of the distal section 110 of the tubing 102. In the illustrated embodiment, the distal section 110 is creased and folded inwards to decrease its effective diameter, and inserted into the restraint section 210. As discussed above, the restraint section 210 restrains the distal section 110 of the percutaneous access sheath 100 in its smaller cross-sectional profile. The restraint section 210 may be approximately the same length as or shorter than the distal section 110. In the illustrated embodiment, the restraint section 210 is approximately 11-24 cm.

As will be explained in more detail below, in some embodiments, the jacket 200 is removed from the access sheath 100 and the surgical site after the sheath 100 is expanded. In other embodiments, the jacket 200 is attached to the sheath 100 and remains attached to the sheath 100 after it is expanded and during the surgical procedure. In such latter embodiments, the jacket 200 may be securely attached to the access sheath by, for example, at least one adhesive or heat bond, preferably extending axially along a section of the access sheath 100 generally opposite the folds or creases.

In certain embodiments a jacket 200 may not be necessary if the distal section 110 of the percutaneous access sheath 100 is made of an expandable material that may be stretched from a first, smaller cross-sectional profile to a second, larger cross-sectional profile. In these embodiments, the outer surface of the distal section 110 is preferably made of a smooth material to facilitate the insertion of the percutaneous access sheath 100 into a treatment site. In still other embodiments, the jacket 200 may be a stretchable material that may be stretched with or without elastic deformation from a first, smaller cross-sectional profile to a second, larger cross-sectional profile as the sheath is expanded.

FIG. 4 is an overview of the deployment catheter 300. It is provided with an expansion element such as balloon 310. Referring to FIGS. 1, 1A and FIG. 4, the deployment catheter 300 is inserted into the lumen 108 of the percutaneous access sheath 100 such that the balloon 310 is arranged within the distal section 110. The balloon 310 may then be inflated to expand the distal section 110 from its first, smaller cross-sectional profile to its second, larger cross-sectional profile following the insertion of the percutaneous access sheath 100 into a treatment site.

With particular reference to FIG. 4, an inner tube 302 extends the entire length of the deployment catheter 300. A guide wire lumen 304 is defined by the interior of the inner tube 302. The deployment catheter 300 can travel along a guide wire extending through the guide wire lumen 304. The inner tube 302 can carry coaxially on its exterior an outer tube 306. The outer tube 306 terminates proximally into the distal end of a y-connector 308, and distally into a balloon 310 such that the space or annulus between the two tubes 302 and 306 forms an inflation lumen for the balloon 310. The balloon 310 may be made of any of a variety of suitable materials, such as, but not limited to, PET, copolymers of polyester, Nylon, PEBAX, Polyurethane, and copolymers of urethane. The Y-connector 308 may be provided with an optional support tube (not shown) extending from its distal end and over a proximal section of the outer tube 306, to increase the rigidity of the deployment catheter 300 during insertion. This support tube may be made of any of a variety of materials, such as, a stainless steel hypotube. Alternatively, the two catheter tubes 302 and 306 can be replaced by a single multi-lumen tube with one lumen capable of passing a guidewire therethrough and another lumen capable of inflating the balloon through scythes or fenestrations placed through the tubing wall inside the balloon and operably connecting the balloon interior to the balloon inflation lumen. In such an embodiment, the distal end of the balloon inflation lumen of the multi-lumen tube may be advantageously plugged or sealed to prevent the escape of pressure from the balloon. The proximal end of the balloon inflation lumen may, in turn, terminate and be operably connected with the sideport of the Y-connector 308.

FIG. 5 is an enlarged view of the distal end 314 of the exemplary embodiment of the deployment catheter 300. Both the inner tube 302 and the guide wire lumen 304 extend through the distal end 314 of the balloon 310. In the illustrated embodiment, the distal end 314 of the balloon 310 necks down and is attached to a tip 315 at a sealing portion 317. The tip 315, in turn, may extend over the distal end of the inner tube 302. The inner tube 302 may carry coaxially on its exterior a pair of marker rings 316a, 316b near the distal end 314 of the balloon 310. With reference to FIG. 8, the pair of markers 316a, 316b are spaced apart such that when the deployment catheter 300 is inserted into the lumen 108 and expanded they correspond to the distal edge 105a and proximal edge 105b of the beveled distal face 111 (see FIG. 1). In a modified arrangement, the markers 316a and 316b may be carried by the distal end 314 of the balloon 310. The markers 316a and 316b may be made of gold, tantalum, platinum or another radio-opaque material suitable for visualization under fluoroscopy. Additional markers may be provided on the deployment catheter to aid in visualizing its location. In another embodiment, the markers 316a and 316b may be replaced with a single axially elongated marker having a leading and trailing edge that corresponds to the distal edge 105a and proximal edge 105b of the beveled distal face 111.

With reference to FIG. 4, a balloon inflation lumen 318, defined in the space between the inner tube 302 and the outer tube 306, communicates with the interior of the balloon 310. As discussed above, the balloon 310 may be inflated to expand the distal section 110 of the percutaneous access sheath 100 from its first, smaller cross-sectional profile to its second, larger cross-sectional profile. Thus, the length of the balloon 310 is approximately equal to or slightly longer than the length of the distal section 110. In the illustrated embodiment, which is configured for percutaneous nephrostomy, the length of the balloon 310 is approximately 12.5 cm. For other clinical applications, the length of the balloon 310 may be in the range of about 8-90 cm.

Figure 6:
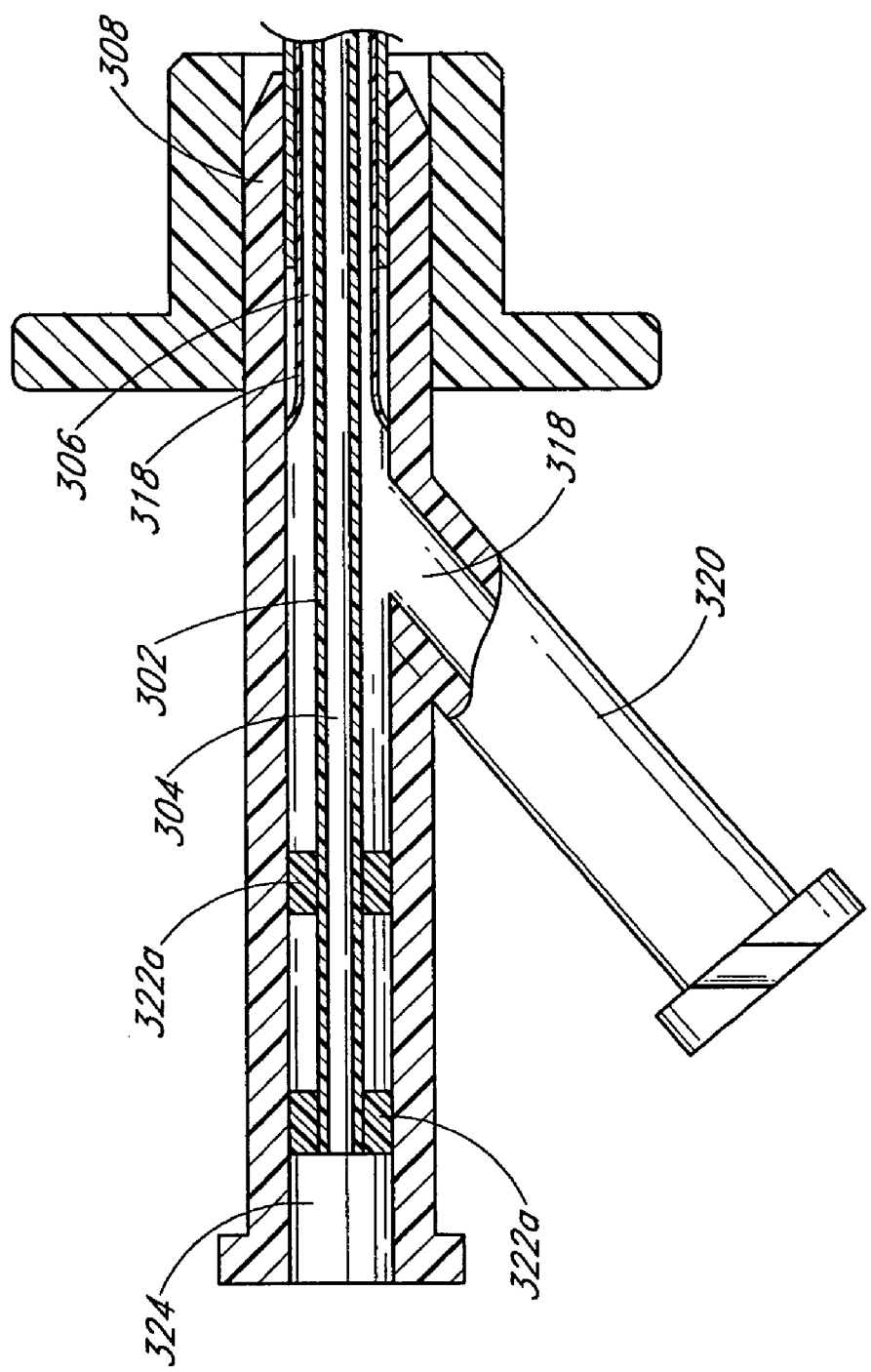
FIG. 6 is an enlarged view of the proximal end of the expansion balloon catheter.

FIG. 6 is an enlarged view of the proximal end of the illustrated embodiment of the deployment catheter 300. Both the inner tube 302 and the guide wire lumen 304 extend through to substantially the distal end of the y-connector 308. The Y-connector 308 may have a hole or lumen that operably connects to the guidewire lumen 304 to permit complete through passage of the guidewire or other material. The balloon inflation lumen 318, defined in the space between the inner tube 302 and the outer tube 306, opens into an inflation port 320 in the Y-connector 308. The illustrated embodiment uses a pair of stoppers 322a, 322b to align the inner tube 302 within the Y-connector 308 and prevent the balloon inflation lumen 318 from communicating with the space 324 in the main branch of the Y-connector 308. Thus, only the inflation port 320 communicates via the balloon inflation lumen 318 with the interior of the balloon. A pump (e.g., a syringe pump) may be connected to the inflation port 320 to inflate or deflate the balloon 310. In a modified embodiment, an inflation device or pump (e.g., a syringe pump) may be pre-attached or integrally formed with the port 320. The inflation device (not shown) may be pre-loaded with inflation material. To enable visualization of the state of the balloon 310, it may be inflated with contrast media. Suitable inflation materials include, but are not limited to, saline, water, gas, contrast media such as Renografin® or Omnipaque®, or the like. The inflation material is preferably sterile to minimize the risk of infection should a fluid leak occur.

FIG. 7 illustrates the percutaneous access sheath assembly 150 in a collapsed or smaller profile configuration. The percutaneous access sheath assembly 150 comprises the percutaneous access sheath 100, the jacket 200 and the deployment catheter 300. It is assembled by inserting the deployment catheter 300 into the percutaneous access sheath 100 and inserting the percutaneous access sheath 100 into the jacket 200 such as via the slit 206 or other proximal opening provided near its proximal end 202. The balloon 310, which is not shown in FIG. 7, of the deployment catheter 300 is deflated, folded and inserted into the distal section 110 of the access sheath 100. The distal section 110, as discussed above, is creased and folded inwards to decrease its effective diameter, and inserted into the restraint section 210 of the jacket 200. As discussed, the balloon 310 is approximately the same length as or just longer than the distal section 110 and the restraint section 210.

FIG. 5A illustrated a modified embodiment of the distal end 314' of percutaneous access sheath assembly 150. Referring to FIGS. 3 and 5A, in this embodiment, the sheath assembly 150' includes a stop 350 for limiting the distal advance of the jacket 200 in response to force from the inflating balloon 310. Referring to FIGS. 4 and 5A, the stop 350 may be configured in a variety of ways, such as the distal stop 350, which is coupled to the deployment catheter 300. As the balloon 310 is expanded, the radial expansion of the balloon 310 may push the jacket 200 (see FIG. 7) distally over the distal end of the balloon 310. This may prevent the distal end of the jacket 200 from being fully torn or separated. The distal stop 350 is configured to substantially prevent or reduce this distal migration of the jacket 200 as the balloon 310 is expanded.

With reference to the illustrated embodiment, the distal stop 350 may be integrally molded into or attached to the distal end of the balloon 310. The stop 350 includes a proximally facing surface 352, which may contact the distal end of the jacket 200 to prevent distal movement. Referring to FIG. 5A, the outer surface of the stop 354 is preferably tapered from its distal end to the proximally facing surface 352 such that during assembly the distal tip 210 of the jacket 200 may be pulled proximally over distal stop 350.

In a modified embodiment, the distal stop 350 may comprise a separate component that is coupled to the balloon 310 or to the deployment catheter 300. For example, the stop 350 comprises a section of tubing or ring that has been bonded or otherwise coupled to the distal end 314 of the deployment catheter 310. The tubing may be formed of PET, Hytrel or other suitable materials. In another embodiment, the distal stop 350 is formed form a section of tubing that may be heat shrunk onto the distal end 314 of the deployment catheter 300.

FIG. 5B illustrates another embodiment of the distal end 314" for reducing the migration of the jacket 200. In this embodiment, the shape of the distal end 314" of the balloon 310 is modified to reduce axial force vectors on the jacket 200 as the balloon 310 is expanded. In the embodiment shown in FIG. 5B, the distal end 314" of the balloon 310 includes a substantially cylindrical section 360, which is generally positioned adjacent the sealing portion 317 and under the distal end of the jacket 200. A tapered section 364 lies proximal to the cylindrical section 360. This arrangement produces primarily radial force vectors at the distal tip of the jacket 200 as the balloon 310 is expanded and advantageously reduces distal migration of the jacket 200. In a modified embodiment, the substantially cylindrical section 360 may alternately include a distal cylindrical taper 366 that may or may not be less than the taper of the tapered section 364. For example, in one embodiment, the distal taper end 366 of the substantially cylindrical portion 360 tapers at an angle of between about 1 degree to about 90 degrees and preferably to about 30 degrees to about 60 degrees and the tapered section 364 tapers from an angle of about 1 degree to about 90 degrees and preferably to about 30 degrees to 60 about degrees.

FIG. 8 illustrates the percutaneous access sheath assembly 150 in an expanded or larger profile configuration. In the expanded configuration, the jacket 200 has been removed and the balloon 310 has been inflated to expand the distal section 110 of the access sheath 100. The proximal end of the deployment catheter 300 is shown protruding out the proximal end of the sheath assembly 150.

One exemplary embodiment of use will now be described with reference to FIGS. 9-12, which discloses a schematic representation of a kidney 10. In particular, the kidney 10 includes a central cavity, the renal sinus 12, which contains the upper part of the renal pelvis 14 and the calyces 16. The calyces 16 are cup shaped tubes, which may vary from seven to thirteen in number and unite to form two or three short tubes that, in turn, join to form the funnel-shaped renal pelvis 14. The renal pelvis 14 communicates with the ureter 18, which is partly outside the renal sinus 12. The renal calyces 16 and pelvis 14 together form the upper expanded end of the excretory duct or renal collection system of the kidney 10. The kidney 10 is composed of an internal medullary and cortical substance 20. A renal capsule 22 covers the kidney 10.

Figure 9:
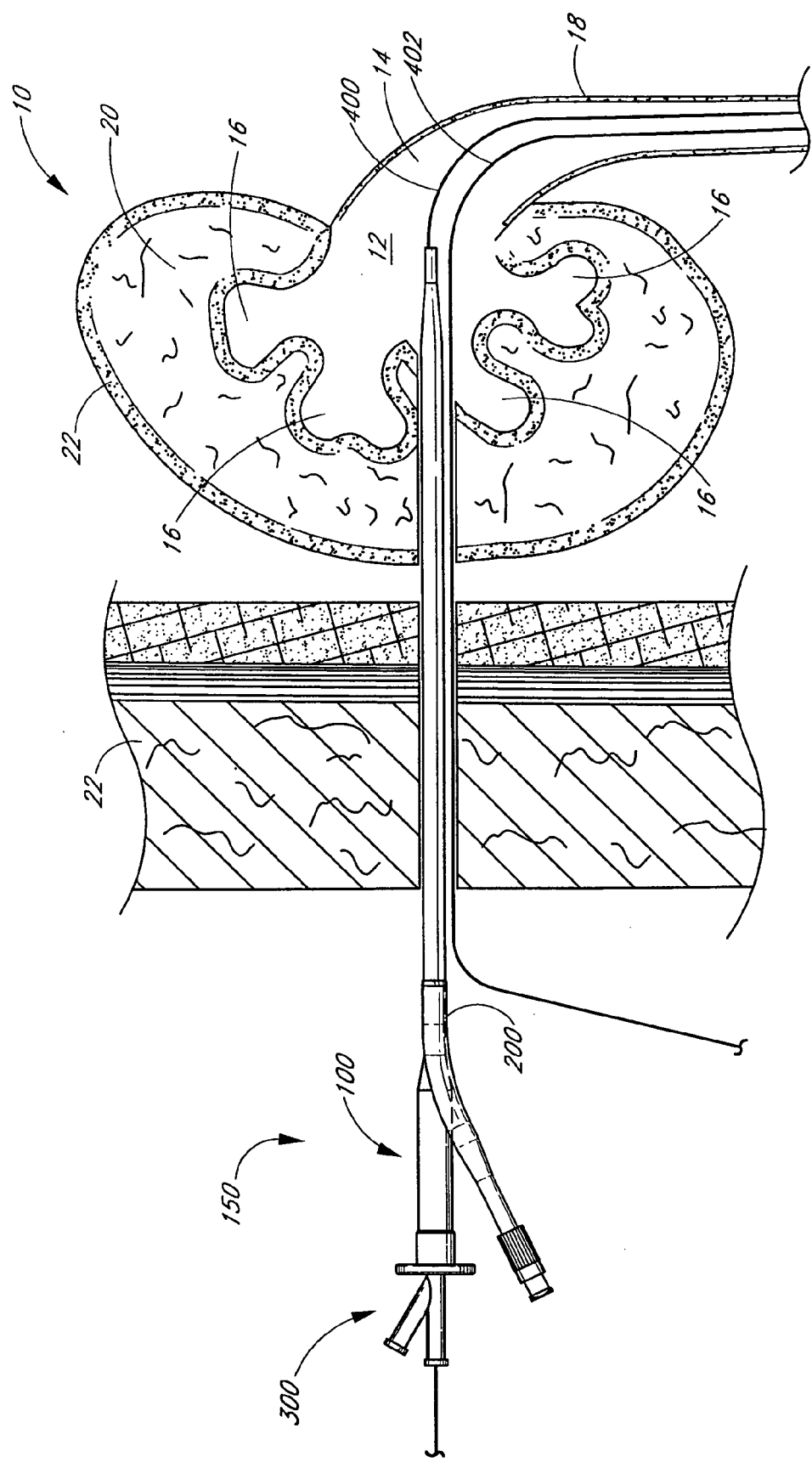
FIG. 9 illustrates the percutaneous access sheath assembly of FIG. 7 inserted into a renal calyx of a kidney, in a first, low profile configuration.

As shown in FIG. 9, a guidewire 400 may be placed through the skin and connective tissue 22 into the renal collection system 12. In one embodiment, the guidewire 400 is inserted through the renal parenchyma and the ureter using fluoroscopic control. The guidewire 400 may be 0.038" stiff guidewire that is inserted through a small (e.g., 1.7 to two centimeter) incision made at the guidewire skin entry cite. A second "safety wire" 402 may be placed with a dual lumen catheter (not shown) for maintaining the tract should the first wire become dislodged or kinked. Guidewire sizes ranging from 0.020 inches to 0.045 inches in diameter may be appropriate for such procedures.

Figure 9A:
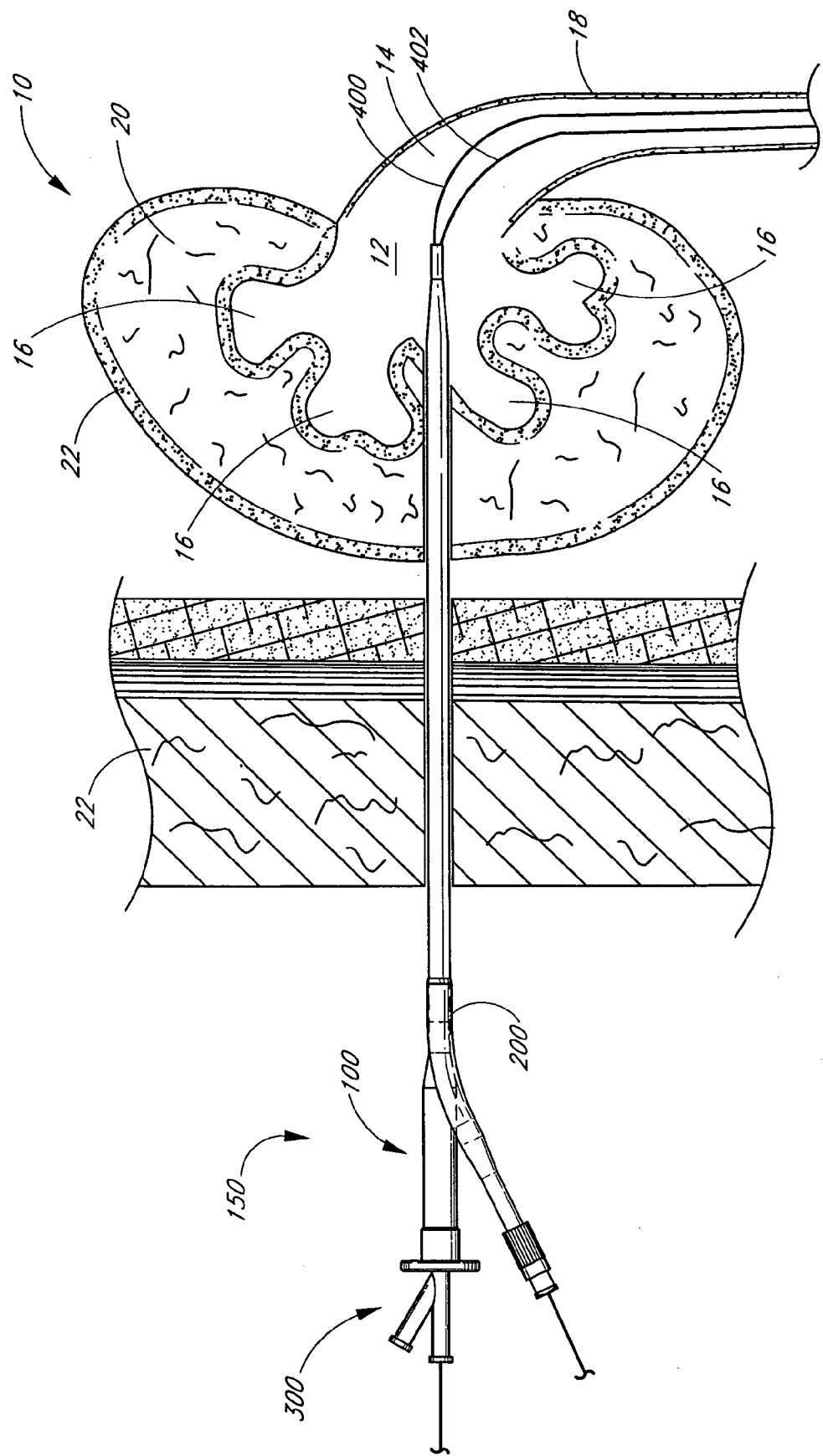
FIG. 9A illustrates a modified embodiment of the percutaneous access sheath assembly of FIG. 7 inserted into a renal calyx of a kidney, in a first, low profile configuration.
Figure 10:
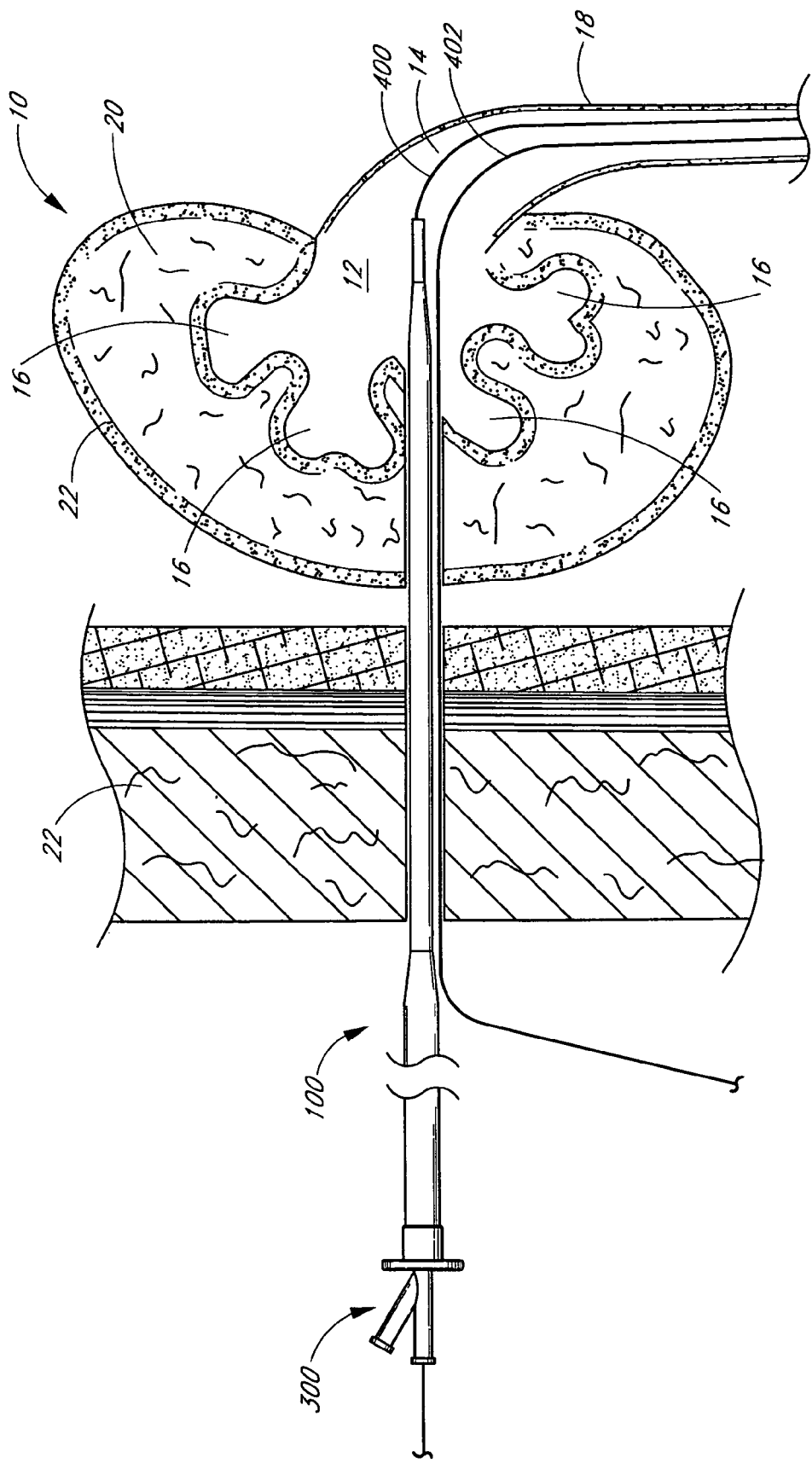
FIG. 10 illustrates the percutaneous access sheath assembly of FIG. 9 with the jacket removed.

The guide wire 400 may be inserted into the guide wire lumen 304 (see FIG. 4) of the deployment catheter 300 of the percutaneous access sheath assembly 150. The entire assembly 150 may travel over the guide wire 400 until its distal tapered portion is positioned just within the renal pelvis. As mentioned above, the distal tip 314 is preferably provided with a pair of radiopaque tip markers 316a, 316b to aid placement. The jacket 200, which is on the exterior of the percutaneous access sheath assembly 150, facilitates the insertion because of its smooth, low profile exterior. As mentioned above, in a modified embodiment shown in FIG. 9A, the second safety wire 402 may be positioned within the secondary lumen 217 (see FIG. 2A) provided in the jacket 200'. In this manner, the second safety wire 402 may placed when the assembly 150 is advanced over the guide wire 400. The second safety wire 402 is released when the jacket is removed as described below. In a modified embodiment, the secondary wire 402 may be placed between the sheath 100 and the jacket 200.

Following the insertion of the percutaneous access sheath assembly 150, the access sheath 100 may be expanded and released from the jacket 200. This may be accomplished by inflating, at least partially, the balloon 310 (not visible in FIG. 10) and radially expanding the access sheath 100 until the jacket 200 separates, preferably along the longitudinal axis of the jacket 200. As discussed above, the balloon 310 is arranged within the distal section 110 of the percutaneous access sheath 100, which is itself arranged within the restraint section 210 of the jacket 200. Thus, inflating the balloon 310 causes the distal section 110 of the percutaneous access sheath 100 to expand, tearing or separating the restraint section 210 of the jacket 200 preferably along its longitudinal axis.

Figure 11:
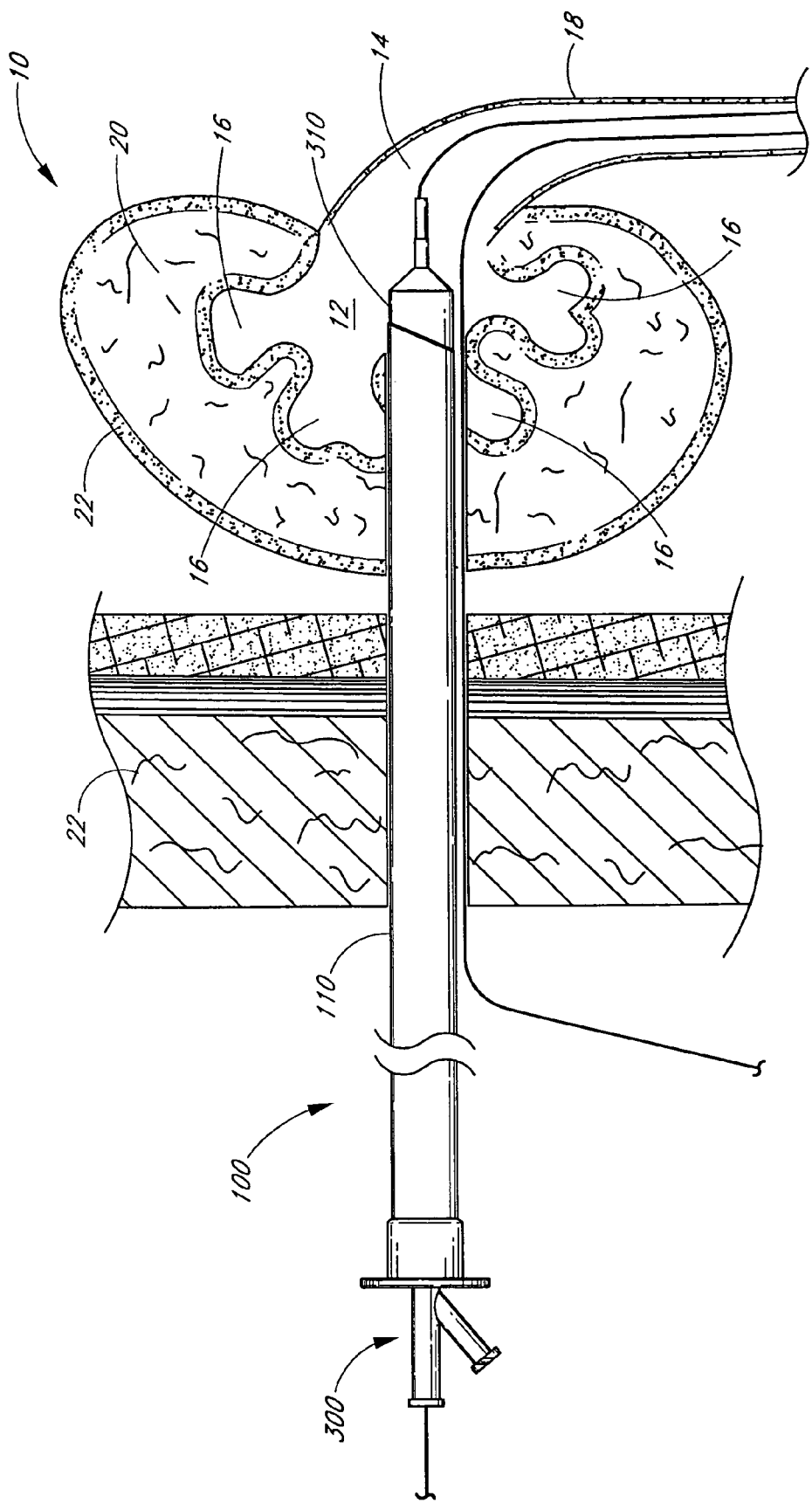
FIG. 11 illustrates the percutaneous access sheath assembly of FIG. 10 with the jacket removed and the expansion catheter fully expanded in a second, functional configuration.

As shown in FIG. 11, after the sheath 100 is released from the jacket 200, the balloon 310 may be fully inflated to expand the distal section 110 of the percutaneous access sheath to its full cross-sectional profile. In one embodiment, the balloon 310 is inflated by providing a pump (e.g., a high pressure balloon inflation syringe) with about 20-25 cc or more of a diluted contrast media (e.g., a 50% solution of Renografin® and sterile saline). After removing the air from the pump and associated tubing, the pump may be attached to the inflation/deflation port of the central balloon shaft. Preferably, under fluoroscopic control, the dilute contrast media is slowly injected until a maximum pressure of about 12 to 25 bar is achieved. Inflation pressure is preferably maintained for a minimum of about 60 seconds to reduce or eliminate any "waist" (i.e., partially unexpanded sections) that may remain along the length of the expanded sheath 100.

In some embodiments, after the sheath 100 has been released from the jacket 200, the jacket 200 may be removed from the access sheath 100 and the surgical site. In other embodiments, the jacket 200 may remain attached to the access sheath 100 during use. As explained above, in such embodiments, the jacket 200 may be securely attached to the access sheath by, for example, an adhesive or heat bond.

After the balloon 310 is inflated, it may be deflated to ease the removal of the deployment catheter 300. As discussed above, the inflation and deflation of the balloon 310 may be done via a pump connected to the port 320 of the deployment catheter 300, and preferably with a dilute radiopaque contrast media being pumped, to better convey the state of the balloon to an observer by way of fluoroscopic imaging.

In another embodiment, the access sheath 100 may be sequentially expanded. For example, in one embodiment, the length of the balloon 310 is smaller than the length of the access sheath 100. In such an embodiment, the access sheath 100 may be expanded in sections as the balloon 310 is sequentially deflated, advanced or withdrawn and then re-inflated to expand other sections of the access sheath. The access sheath 100 may be sequentially expanded from the proximal end to the distal end or from the distal end to the proximal end.

Figure 12:
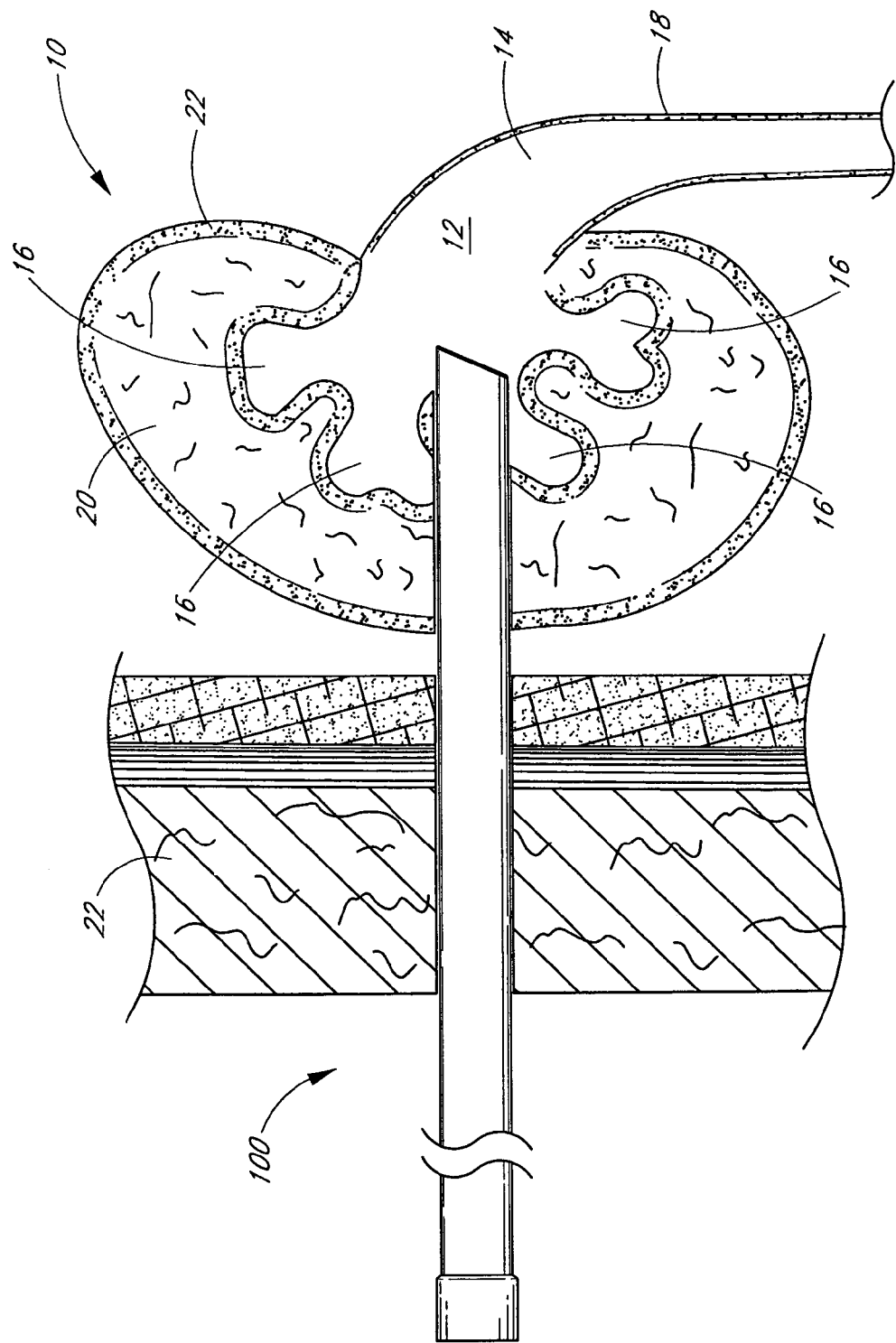
FIG. 12 illustrates the percutaneous access assembly of FIG. 11 with the expansion catheter removed.

As shown in FIG. 12, with the deployment catheter 300 (not shown) removed, the percutaneous access sheath 100 extends into the renal pelvis 14 and provides a working lumen for instrumentation or inspection. The establishment of this working lumen may provide access for several procedures such as biopsy, stone extraction, antegrade endopyelotomy, and resection of transitional cell carcinoma of the upper urinary tract. Referring to FIGS. 1 and 12, in the embodiments with a beveled edge 111, the leading edge 105a maintains positional purchase within the target tissue or organ while the trailing edge 105b provides the sheath 100 with an aperture to facilitate instrument maneuvering and visualization within the internal structure of the tissue or organ under examination or repair.

In some applications, it may be desirable to lengthen the working lumen after the access sheath 500 has been wholly or partially deployed. For this purpose, FIG. 13A illustrates the proximal end of a modified embodiment of a percutaneous access sheath 500, which includes an extender coupling 502 for extending the length of the working lumen 108.

In the illustrated embodiment, the extender coupling 502 is positioned within the proximal section 103 of the access sheath 500. A short proximal portion 506 may be removably coupled to the coupling extender 502. The extender coupling 502 and the short proximal portion 506 preferably include corresponding retention structures for removably coupling these two components 502 506 together. Any of a variety of complementary retention structures may be provided between the extender coupling 502 and the short proximal portion 506 for releasably coupling these two components. These structures may include, but are not limited, hooks, latches, prongs, interference fit, press fit, bayonet mounts, threads, and the like. In the illustrated embodiment, the corresponding retention structures comprise corresponding threads 508a and 508b formed on the inner and outer surfaces of the coupling extender 502 and short proximal portion 506 respectively. Threads 508a, 508b may comprises a complete 360-degree revolution about the corresponding part or less than a full revolution such as in a Luer lock or other quick connect configuration.

Figure 13A:
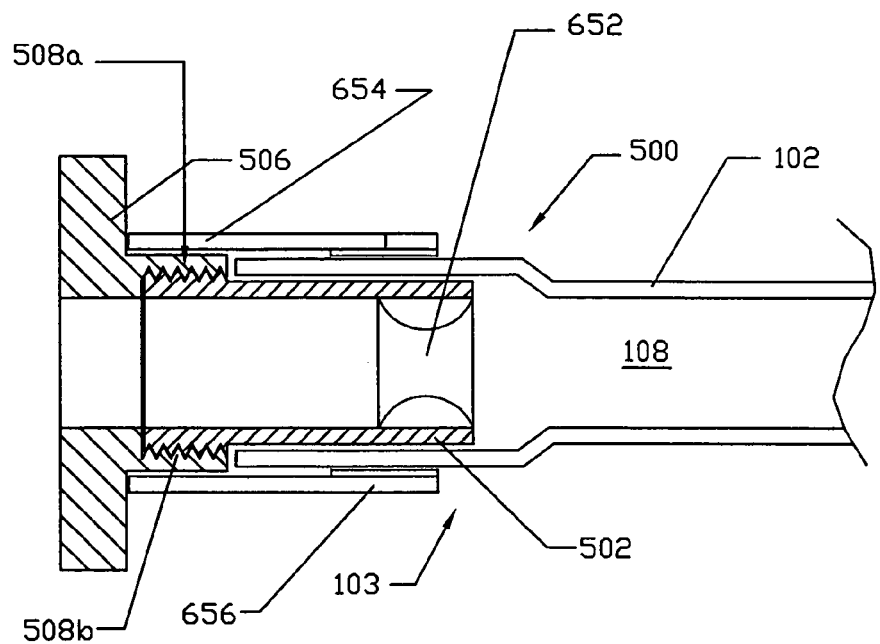
FIG. 13A illustrates the proximal end of the percutaneous access sheath assembly of FIG. 7 in combination with an extender coupling.

With continued reference to FIG. 13A, the illustrated access sheath 500 optionally includes an instrumentation valve 652 and/or a sealing sleeve 654. The sealing sleeve 654 advantageously provides a seal between the short proximal portion 506 and the exterior of the tubing 102. In the illustrated embodiment, the sleeve 654 comprises a generally tubular body which is coupled to the distal end of the short proximal portion 506 and extends over the junction between the short proximal portion 506 and the coupler 502 as shown in FIG. 13A. A sealing member 656 is positioned on the sleeve 654 between the outer surface of the tubing 102 and the sleeve 654. In one embodiment, the sealing member 656 is configured to slide over the proximal end 103 of the tubing 102 as the short proximal portion 506 is coupled to the coupler 502. In this manner, the sealing member 656 forms a seal between the sheath tubing 102 and the sleeve 654 to prevent or reduce fluid escape through the threaded areas 508a, 508b. The sleeve 654 and the sealing member 656 may be made of any of a variety of materials, such as, for example, C-flex, polyurethane, silicone elastomer, PTFE, latex rubber, polyethylene, polypropylene, or the like. In other embodiments, the sealing member 656 may be integrally formed with the sleeve 654 and/or the sealing member 656 may be formed on the proximal end 103 of the tubing 102. In another embodiment, the sleeve 654 may be coupled or integrally formed with the proximal end 103 of the tubing 102.

Figure 13B:
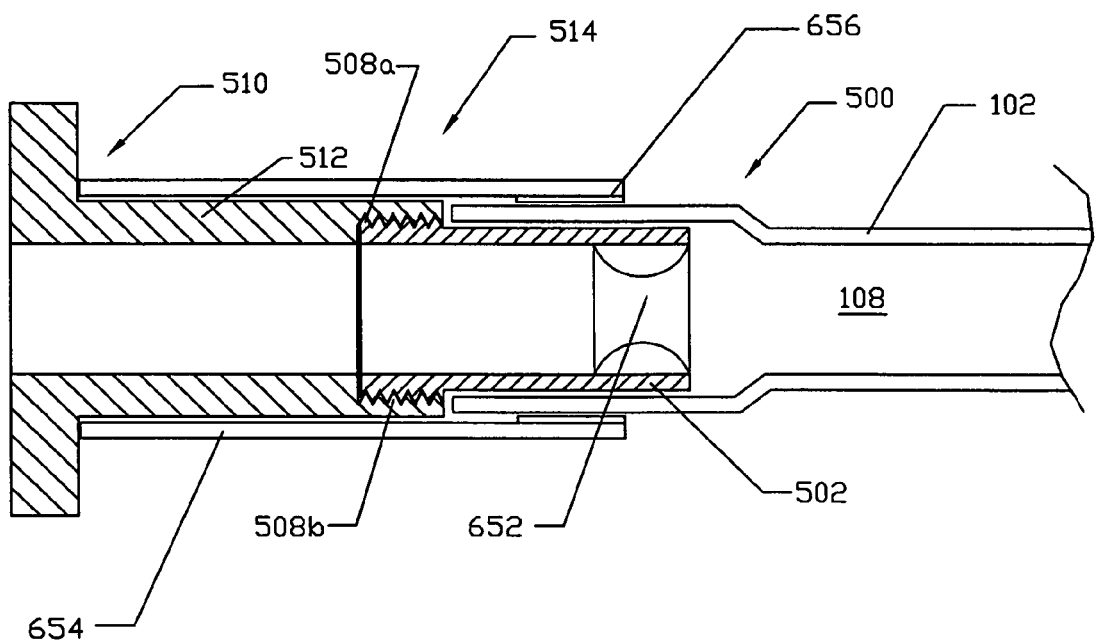
FIG. 13B illustrates the proximal end of the percutaneous access sheath assembly as in FIG. 13A in combination with an extender.

In the illustrated embodiment, the instrumentation valve 652 positioned within the coupler 502 and is configured to prevent or reduce the escape of fluids between the coupler 502 and any instrumentation, which might be inserted therethrough. Any of a variety of structures may be used to prevent or reduce the escape of fluids between the coupler 502 and any instrumentation inserted therethrough, such as, for example, duck bill valves, Touhy-Borst valves, donut valves, diaphragms with a central slit or hole and the like. The instrumentation valve 652 may be made from any of a variety of materials, such as, for example, C-flex, polyurethane, silicone elastomer, PTFE, latex rubber, polyethylene, polypropylene, or the like. As mentioned above, the instrumentation valve 652 is advantageously configured to provide a seal around the outside of any instrumentation passed therethrough and may further seal to itself without the need for any cylindrical or axially elongate instrumentation, such as a catheter, being inserted therethrough. The use of the instrumentation valve 652, located distally to the threaded area 508a and 508b as illustrated in FIGS. 13A and 13B, may reduce or eliminate the need to provide a seal against fluid loss at the point of the threaded area 508a, 508b. Thus, in some embodiments, the sleeve 654 and the sleeve sliding seal 656 may be eliminated or replaced.

FIG. 13B illustrates a lengthened access sheath 500. To increase the length of the working lumen, the short proximal portion 506 may be removed and an extender 510 having a length longer than the short proximal portion 506 may be attached to the coupling extender 502. In the illustrated embodiment, the extender 510 comprises a generally tubular body 512 with a distal end 514 and a proximal end configured with a complementary retention structure (e.g., threads 508a and 508b in the illustrated embodiment) for releasably engaging the coupling extender 502. The access sheath 500 may also comprise an instrumentation valve 652, a length of expandable sheath tubing 102, and an optional sealing sleeve 654, which further comprises a sleeve sliding seal 656.

In this manner, by coupling the extender 510 to the coupling extender 502, the length of the working lumen 108 may be increased allowing the surgeon to advance the distal end of the access sheath 500 further into the patient. In a modified embodiment, the coupling extender 502 may be integrally formed with the access sheath 500. In addition, the surgeon may be provided with more than one length of extender 510. In addition, the proximal end of the extender 510 may be configured such that it can be coupled to a second extender (not shown). The extender 510 and/or the short distal portion 506 may also be provided as part of a kit with the assembly 150. In this embodiment, the extender 510 is releasably affixed to the proximal end of the access sheath 500 by way of threaded attachment, but such attachment may also be accomplished by way of latches, snaps, bayonet mounts, and the like. As shown in FIG. 13B, the extender 510 may also include a sleeve 654 and sealing member 656 configured as described above to provide a seal between the extender 510 and the coupler 502.

Figure 13C:
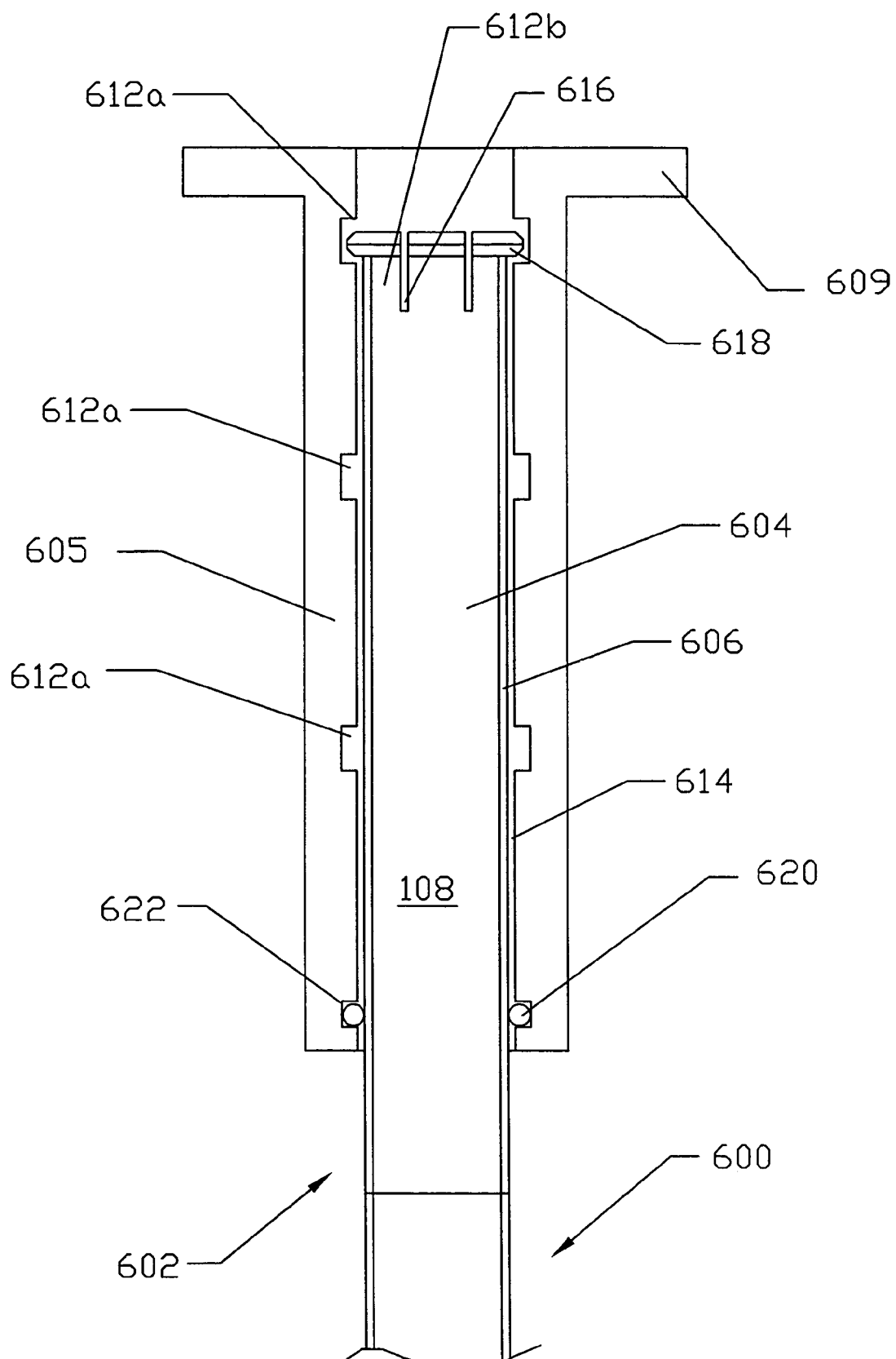
FIG. 13C illustrates the proximal end of the percutaneous access sheath assembly of FIG. 7 with a telescoping member.

FIG. 13C illustrates another embodiment for increasing the length of the working lumen 108 after an access sheath 600 has been wholly or partially deployed. In this embodiment, the proximal end 602 of the access sheath 600 is coupled, for example using threads or a bayonet mount, or integrally formed with an inner telescoping member 604, which comprises an elongated tubular body 606. An outer telescoping member 605 is positioned over the inner telescoping member 604 and further comprises a flange 609 positioned at the proximal end of the outer telescoping member 605. As shown in FIG. 13C, in a first position, the inner and outer telescoping members 604, 605 overlap each other to provide a working lumen of a first, shorter length. By withdrawing the outer telescoping member 605 and reducing the overlap between the two components 604, 605, the length of the working lumen 108 may be extended.

The inner telescoping member 604 and the outer telescoping member 605 preferably include corresponding structures 612a, 612b for limiting the axial movement between the inner and outer telescoping members 604, 605. Any of a variety of corresponding structures may be provided between the inner telescoping member 604 and the outer telescoping member 605 for limiting axial movement between these components. These structures may include, but are not limited, threads, latches, prongs, interference fit, press fit and the like. In the illustrated embodiment, the corresponding structures comprise one or more lateral or circumferential grooves or indentations 612a formed on the inner surface 614 of the outer telescoping member 605 and lever arms 612b with a cantilever spring effect formed on the proximal end of the inner telescoping member 604. In of a variety of ways may be used to create a cantilever spring effect for the lever arms 612b. For example, in the illustrated arrangement, the lever arms 612b lie between slots 616 extending from the proximal end of the inner member 604. However, those of skill in the art will recognize that the slots 616 are only one of many ways to create a cantilever spring effect in the lever arms 612b. The lever arms 612b may also comprise radially extending protrusions 618. The extending protrusions 618, the edges of the indentations 612a, or both, may be beveled or rounded to permit the lever arms 612b to deflect inward when an axial force is applied to change the length of the sheath 600. With reference to FIG. 13C, in the first position, the lever arms 612b engage the proximal most indentation 612a of the outer member 605 thereby securing the axial position of the inner and outer members 604, 605. To lengthen the working lumen 108, sufficient proximal force is applied to the outer member 605, against an opposite force applied to the proximal end 602 of the access sheath 600, to cause the lever arms 612b to deflect inwardly allowing the outer member 605 to move proximally with respect to the inner member 604. The outer member may be withdrawn until the lever arms 612b engage a more proximal indentation 612a. In this manner, the length of the working lumen may be increased, or decreased by movement in the opposite axial direction. A sealing member 620 (e.g., an O-ring) is preferably provided between the inner and outer members 604, 605. In the illustrated arrangement, the sealing member 620 is positioned within a circumferentially disposed recess 622 positioned on the inner diameter and near the distal end of the outer member 605.

FIGS. 13D and 13E illustrate another embodiment for increasing, or decreasing, the length of the working lumen 108 after an access sheath 600 has been wholly or partially deployed. The proximal end of the sheath 600 may be coupled, using threads, bayonet mounts, etc., or it may be formed integrally with the length changing structures. As with the previous embodiment, this embodiment includes inner and outer telescoping members 604, 605 with corresponding structures 612a, 612b. In this arrangement, the structure 612b on the inner member 604 comprises one or more tabs 612b, which engage threads 618a formed on the inner surface of the outer member 605. Threads 618a may comprise a complete 360-degree revolution about the corresponding part or less than a full revolution such as in a Luer lock and/or other combinations of radial and axial grooves. In an embodiment, there are between 2 and 20 complete 360-degree turns to cause the tabs 612b to traverse the length of the outer member 605. The inner member 604 may further comprise one or more slots 670 running parallel to the longitudinal axis of the inner member 604 and disposed on the inner diameter of said inner member 604 to provide a quick release connection. The elongating structure comprises an extender tube 650 that terminates at its proximal end with an enlarged region 651 suitable for gripping. The extender tube 650 may further comprise an instrumentation valve 652 as described above. The extender tube 650 may further comprise one or more radially outwardly directed pins or fins 672 that engage the slots 670 in the inner member 604. The pins or fins 672 prevent rotation of the enlarged region 651 relative to the access sheath 600 so that instrumentation alignment is maintained while the lengthening or shortening process occurs. To extend the lumen 108, the outer member 605 is rotated with respect to the inner member 604, moving the extender tube 650 and the outer member 605 from the first position, shown in FIG. 13D, to a second, lengthened position as illustrated in FIG. 13E. As the lumen 108 is lengthened, the overlap between the extender tube 650 and outer member 605 and the inner member 604 is reduced. The extender tube 650 preferably rotates relative to the outer member 605 but does not rotate relative to the inner member 604, which is affixed to the access sheath 600.

In some applications, it may be desirable to increase the diameter of the working lumen 108. In one embodiment, a second deployment catheter (not shown) may be provided. The second deployment catheter a includes radially enlargeable expansion structure such as a balloon that has an expanded diameter that is larger than the expanded diameter of the first balloon 310. If it is desirable to expand the working lumen to a diameter that larger than the original expanded diameter, the surgeon may insert the second deployment catheter into the lumen 108 and inflate the balloon to the second larger diameter. The expansion of the second balloon may increase the diameter of the sheath 100 by unfolding or uncreasing additional folds or creases in the access sheath 100. In another embodiment, the sheath tubing 102 may be plastically deformed to a larger diameter. In another embodiment, instead of using the second deployment catheter the, the first balloon 310 of the deployment catheter 300 may be configured to expand to more than one diameter. In another embodiment, an internal plastic sleeve is inserted on the inside of the sheath 100. The internal plastic sleeve serves to limit the expansion diameter of the sheath 100 by the first balloon 310. The internal plastic sleeve is torn or removed after the second, larger balloon catheter 310 is expanded inside the first lumen 108 to permit additional expansion of the working lumen 108.

Figure 14A:
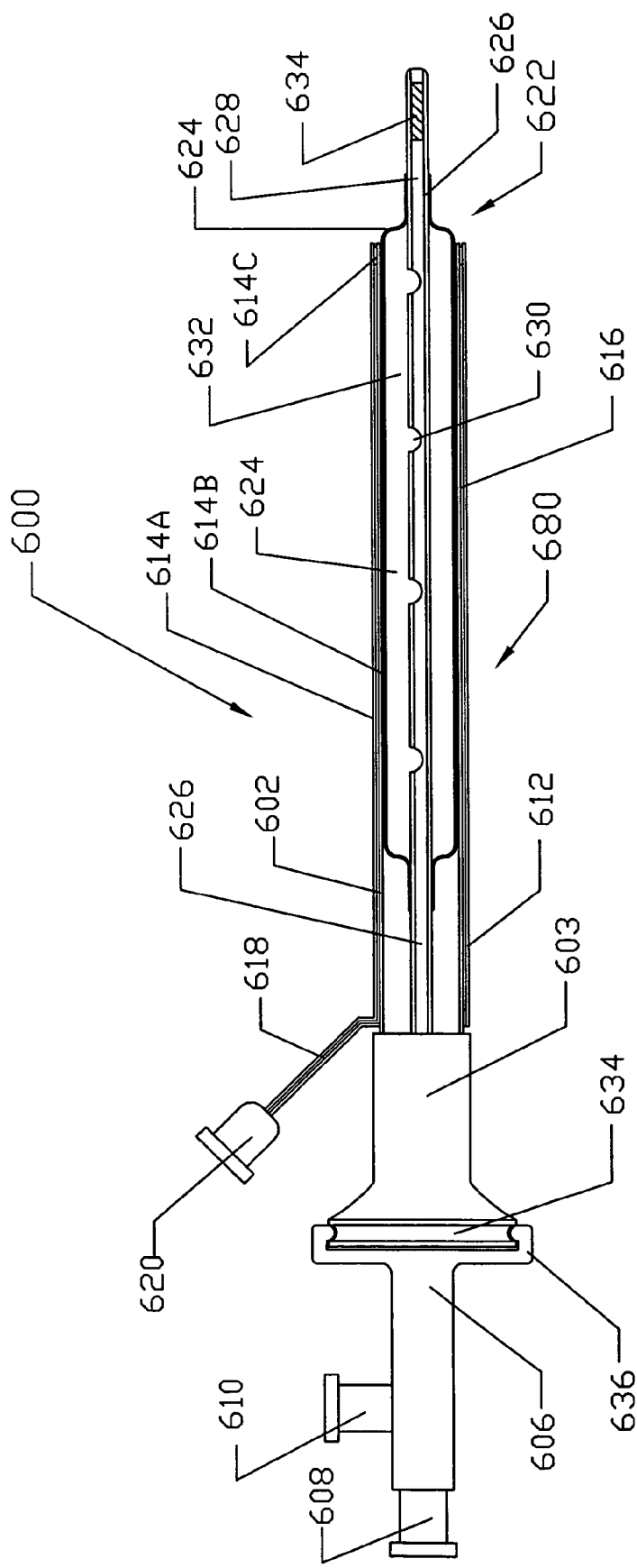
FIG. 14A is a schematic partial cross-sectional view of a modified embodiment of a percutaneous access sheath assembly.
Figure 14B:
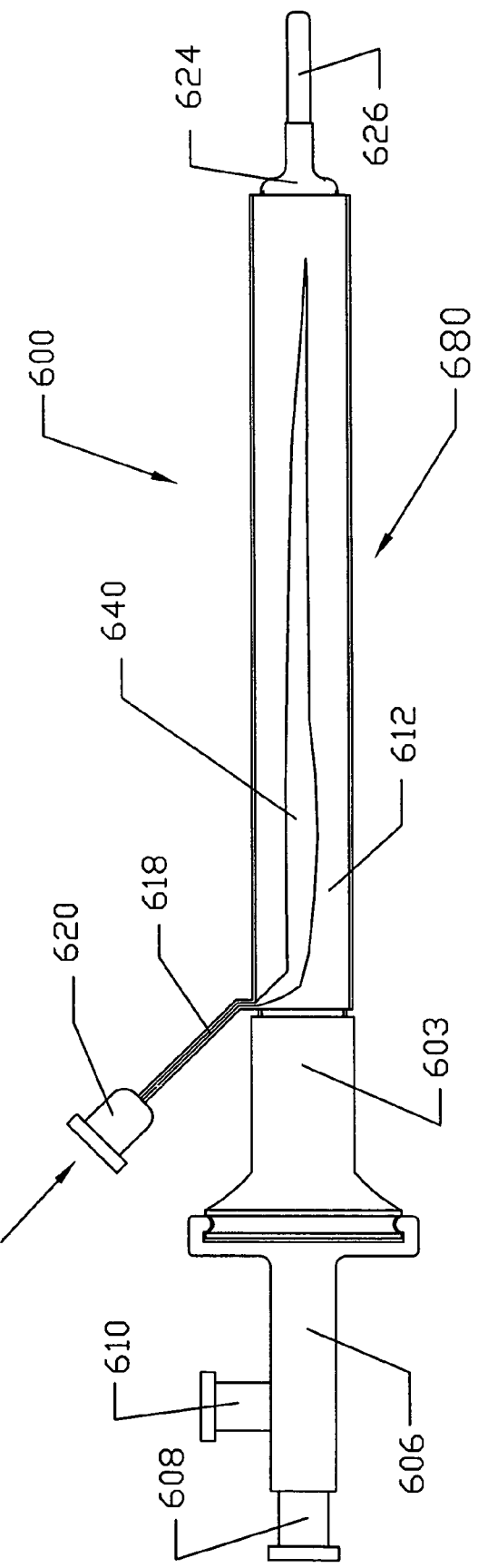
FIG. 14B is a schematic partial cross-sectional view of the percutaneous access sheath assembly as in FIG. 14B with the jacket partially disrupted.

FIGS. 14A and 14B are schematic illustrations of another modified embodiment of an access sheath assembly 680. The assembly comprises an access sheath 600 with a proximal end 602, which may be configured as described previously. The proximal end 602, may be coupled to a proximal hub 603 which may further be coupled to or integrally formed with an inflation hub 606. The inflation hub 606 may include a proximal fitting (e.g., a Luer fitting) 608 and an inflation fitting (e.g. a Luer fitting) 610. The proximal fitting 608 is configured to permit guidewire passage into a through lumen of an expansion assembly 622. The inflation hub 606, in an embodiment, may be connected to the proximal hub 603 using a detent 634 and a clip 636 to permit positive, releaseable engagement. Such releaseable attachment of the inflation hub 606 and the proximal end 604 permits the assembly 680 to be inserted into a patient as a unit, thus providing for greater control during the insertion phase.

The sheath 600 is preferably constrained in a smaller profile configuration by a jacket 612 as described above. In one embodiment, the jacket 612 is configured such that it may be partially or wholly torn by injecting, under pressure, a fluid into the jacket 612. With reference to FIG. 14A, the jacket 612 includes an outer layer 614a, an inner layer 614b and a seal 614c positioned at the distal end of the jacket 612. The outer layer 614a, the inner layer 614b and the seal 614c, define an annulus or lumen 616, which is connected by a conduit 618 to an inflation fitting 620 (e.g., a Luer or Luer lock fitting).

With continued reference to FIG. 14A, the assembly 680 further comprises an expansion assembly 622, which in one embodiment comprises an inflatable balloon 624. The balloon 624 is mounted on a balloon catheter shaft 626, which defines an inflation lumen 628. The shaft 626 may include one or more openings 630 for communicating with the interior 632 of the balloon 624. The openings 630 may be scythed, drilled, or otherwise created openings in the side wall of the shaft 626. The distal end of the inflation lumen 628 may be closed with a sealing valve 634 positioned within, or against, the lumen 628. In this manner, the assembly 680 may be inserted over a guidewire extending through the lumen 628. The guidewire may then be removed from the lumen 628 and the sealing valve 634 may be pushed open through the lumen 628. In one embodiment, the sealing valve 634 may be pushed open with a guidewire. Removal of the guidewire may permit the valve 634 to close. With the distal end of the lumen 628 closed, the balloon 624 may be inflated by injecting an inflation fluid through the balloon inflation fitting 610. Alternative embodiments of this single lumen valved configuration include dual or multiple luen tubes that have separate lumens for guidewires and balloon inflation, or coaxial multiple extrusion designs.

To partially or wholly tear the jacket, inflation fluid, such as water, saline, gas, contrast media, or the like, is injected though conduit 618 into the jacket lumen 616 until the jacket 612 disrupts or forms a tear 640a as shown in FIG. 14B. Such disruption occurs when the pressure within the jacket lumen 616 exceeds the strength of the jacket 612 wall. The jacket 612 may be provided with score lines, thinned regions and the like to promote tearing or disruption in a certain manner (e.g., in certain directions or certain regions). In one embodiment, the inflation fluid may be used to initialize tearing of the jacket 612. After the jacket 612 begins to tear or disrupt, the jacket 612 may be proximally withdrawn to complete the tearing or disruption of the jacket 612. The jacket 612 may then be removed from the sheath 600. In another embodiment, inflation may disrupt the jacket 612 such that the sheath may expand substantially to its fully expanded configuration.

FIGS. 15A-E illustrate another modified embodiment an access sheath assembly 700. In this embodiment, the assembly 700 may include an access sheath 100, jacket 200 and deployment catheter 300 as described above. For simplicity, only the access sheath 100 and the expandable member 310 of the deployment catheter 300 have been illustrated in FIGS. 15A-15E.

With reference to FIGS. 15A-15E, the assembly 700 includes a plurality of releasable retention structures 702 and 704 between the access sheath 100 and the expandable member 310. Any of a variety of releasable retention structures may be provided between the sheath 100 and the expandable member 310. These structures may include, but are not limited to, rails, hooks, latches, prongs, interference fit, press fit and the like. The releasable retention structures are, in an embodiment, axially elongate structures with axial lengths approximating those of the expandable member 310. Provision is made to withdraw the expandable member 310 and its corresponding releasable retention structure proximally to remove the expandable member from the sheath 100. In an embodiment, the expandable member 310 may be reinserted into the sheath 100 and the releasable retention structures realigned and re-engaged. In this embodiment, alignment devices are provided to facilitate correct positioning of the releasable retention structures so that they are easily re-engaged when the expandable member 310 is re-inserted into the sheath 100. Suitable alignment devices include, but are not limited to, keyholes, embossed, raised, or printed markings, or geometries that permit insertion only in one or more pre-determined rotational orientations. In the illustrated embodiment, the releasable retention structures comprise a track member 702, which may be coupled to the sheath 100 by a support member 714, and a rail member 704, which may be coupled to or integrally formed on the outer surface of the expandable member 310. As shown, FIG. 15D, the track member 702 defines a recessed portion 715 that is sized and configured to releasably engage the rail member 704 in a slip or interference fit. In addition, the track member 702 and/or the rail member 704 may be made of an elastic material that permits deformation as the two members engage each other. Preferably, the assembly includes at least two and often at least three pairs of track members 702 and rail members 704 that are spaced across the circumference of the expandable member 310.

With reference to FIGS. 15A and 15B, in use, the expandable member 310 and the sheath 100 may be initially coupled together by the releasable structures 702, 704 when the sheath is in the collapsed, smaller profile configuration. The expandable member 310 may then be expanded to dilate the access sheath 100 as described above. With the sheath 100 expanded, the expandable member 310 may be withdrawn from the access sheath 100 such that the working lumen 108 may be used as described above. In another embodiment, the expandable member need not be initially coupled to the sheath 100 by the releasable structures 702, 704.

When the surgical or diagnostic procedure is complete, the expandable member 310 may be inserted into the access sheath 100 such that the releasable retention structures 702 and 704 engage each other. The expandable member 310 may then be collapsed (e.g., by withdrawing the inflation fluid). The withdrawal of the inflation fluid will result in a radially inwardly directed force on the expandable member 310. As the expandable member 310 collapses, the connection between the structures 702, 704 radially pull the sheath 100 inwardly such that the sheath 100 collapses with the expandable member 310. The expandable member 310 and the access sheath 100 may then be withdrawn from the patient. In this manner, the diameter of the access sheath 100 may be reduced before it is withdrawn from the patient.

In a modified embodiment, a separate collapsible member is provided for collapsing the sheath 100. The collapsible member may be configured as the expandable member 310 described above. In such an embodiment, the collapsible member may include the corresponding structure 704 while the expandable member may be formed without the corresponding structure 704. In another embodiment, the separate collapsible member is different from the expandable member 310 and is used only for collapsing the sheath 100. In this embodiment, the collapsible member may be configured as a collet or other mechanical radial compression device that hooks onto the sheath 100 from the inside.

It will be apparent from the disclosure herein that the percutaneous access assemblies, and/or the methods described herein may also find utility in a wide variety of diagnostic or therapeutic procedures that require an artificially created or natural access tract. For example, the embodiments described herein may be used in many urological applications (e.g., the removal of ureteral strictures and stones, the delivery of drugs, RF devices and radiation for cancer treatment, etc.). In such applications, the percutaneous access sheath 100 may have a length of about 30-300 cm with an unexpanded diameter of about 7-20 French and an expanded diameter of about 14-60 French. The sheath 100 may also be used in many gastrointestinal applications, which require the introduction of a surgical retractor (e.g., to the removal gallstones and appendix procedures). In such applications, the percutaneous access sheath 100 may have a length of about 10-50 cm with an unexpanded diameter of about 3-15 French and an expanded diameter of about 15-60 French. The percutaneous access sheath 100 may also be used as an access catheter for many gastrointestinal applications (e.g., colon therapies, esophageal treatment and the treatment of bowel obstructions). In such applications, the percutaneous access sheath 100 may have a length of about 30-300 cm with an unexpanded diameter of about 7-40 French and an expanded diameter of about 14-120 French.

The sheath may also be used in many cardiovascular applications (e.g., to provide access for minimally invasive heart bypass, valve replacement or the delivery of drugs or angiogenesis agents). In such applications, the percutaneous access sheath 100 may have a length of about 30-300 cm with an unexpanded diameter of about 3-12 French and an expanded diameter of about 5-30 French. For vascular applications (e.g., minimally invasive access to the aorta or contralateral leg arteries for the treatment of, for example, an abdominal aortic aneurysm), the percutaneous access sheath 100 may have a length of about 30-300 cm with an unexpanded diameter of about 5-30 French and an expanded diameter of about 15-75 French. For gynecological applications (e.g., endometrial therapies, delivery of drugs, delivery of cancer agents, sterilization procedures, etc.), the percutaneous access sheath 100 may have a length of about 10-100 cm with an unexpanded diameter of about 3-20 French and an expanded diameter of about 6-60 French.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A method of providing percutaneous access, the method comprising:
   inserting a guidewire into a patient,
   percutaneously inserting an elongate tubular body having a first, smaller cross-sectional profile over the guidewire to a treatment site within the patient, wherein the treatment site is the patient's renal pelvis, the elongate tubular body comprising a distal region, the distal region comprising at least one longitudinal crease and a beveled distal face, the beveled distal face comprising a leading edge and a trailing edge, the at least one longitudinal crease positioned on the distal region generally opposite the side on which the leading edge is positioned wherein the at least one longitudinal crease comprises only two creased outer sections positioned on the perimeter of the distal region and only two creased inner sections positioned within the perimeter of the distal region, wherein the two creased outer sections generally face each other and the two creased inner sections generally face away from each other;
   expanding the elongate tubular body from the first, smaller cross-sectional profile to a second, greater cross-sectional profile by applying radial force by an expandable member positioned within the elongate tubular body;
   removing the expandable member from the elongate tubular body to open a working lumen within the elongate tubular body, the working lumen providing access to the treatment site from outside the patient;
   performing one or more therapeutic procedures at the treatment site through the working lumen;
   collapsing the elongate tubular body to a cross-sectional profile smaller than the second, greater cross-sectional profile; and
   removing the elongate tubular body from the patient.

2. The method as in claim 1, wherein the step of collapsing the elongate tubular body comprises pulling the elongate tubular body in a radially inward direction.

3. The method as in claim 1, wherein the step of collapsing the elongate tubular body comprises inserting a collapsible device into the elongate tubular body and collapsing the collapsible device.

4. The method as in claim 3, further comprising engaging complementary retention structures between the collapsible device and the elongate tubular structure.

5. The method as in claim 3, wherein the step of collapsing the collapsible device comprises deflating a balloon.

6. The method as in claim 3, wherein the expandable member is a balloon.

7. The method as in claim 3, wherein the collapsible device comprises the expandable member.

8. The method as in claim 1, further comprising releasing the elongate tubular body from a constraining tubular jacket, wherein the releasing is accomplished in response to the step of expanding.

9. The method as in claim 1, wherein the therapeutic procedures comprise one or more of a biopsy, stone extraction, antegrade endopyelotomy, resection of transitional cell carcinoma, removal of strictures, and delivery of drugs.

10. The method as in claim 1, wherein the performing one or more therapeutic procedures comprises passing one or more instruments through the working lumen.

11. The method as in claim 10, wherein the one or more instruments comprise a surgical retractor.

12. The method as in claim 10, wherein the second, greater cross-sectional profile of the elongate tubular body reconfigures in response to the passing one or more instruments through the working lumen.

13. The method as in claim 4, wherein the complementary retention structures comprise a track and a rail.

14. The method as in claim 1, wherein percutaneously inserting the elongate tubular body comprises inserting the elongate tubular body and the expandable member positioned within the elongate tubular body as one unit.

15. The method as in claim 14, wherein the elongate tubular body further comprises a proximal hub at its proximal end and the expandable member comprises an inflation hub at its proximal end, the proximal hub and the inflation hub configured to be releaseably engaged, and wherein the removing the expandable member from the elongate tubular body comprises disengaging the proximal hub and the inflation hub.

* * * * *